(12) United States Patent
Xu et al.

(10) Patent No.: US 6,593,122 B1
(45) Date of Patent: Jul. 15, 2003

(54) **METHOD FOR CLONING AND EXPRESSION OF BSERI RESTRICTION ENDONUCLEASE AND BSERI METHYLASE IN *E. COLI***

(75) Inventors: Shuang-yong Xu, Lexington, MA (US); Robert Maunus, Danvers, MA (US); Jack Benner, South Hamilton, MA (US)

(73) Assignee: New England Biolabs, Inc., Beverly, MA (US)

( * ) Notice: Subject to any disclaimer, the term of this patent is extended or adjusted under 35 U.S.C. 154(b) by 7 days.

(21) Appl. No.: 09/975,413

(22) Filed: Oct. 11, 2001

(51) Int. Cl.⁷ .............................. C12N 9/22; C12N 15/55
(52) U.S. Cl. ............... 435/199; 435/320.1; 435/252.33; 536/23.2
(58) Field of Search .............................. 435/194, 320.1, 435/252.33; 536/23.2

(56) References Cited

U.S. PATENT DOCUMENTS

| | | | |
|---|---|---|---|
| 5,200,333 A | 4/1993 | Wilson | 435/172.3 |
| 5,498,535 A | 3/1996 | Fomenkov et al. | 435/172.3 |

OTHER PUBLICATIONS

Roberts and Macelis, Nucl. Acids Res. 27: 312–313, (1999).
Kosykh et al., Mol. Gen. Genet. 178: 717–719, (1980).
Mann et al., Gene 3: 97–112, (1978).
Walder et al., Proc. Natl. Acad. Sci. 78: 1503–1507, (1981).
Bougueleret et al., Nucl. Acids Res. 12: 3659–3676, (1984).
Gingeras and Brooks, Proc. Natl. Acad. Sci. USA 80: 402–406, (1983).
Theriault and Roy, Gene 19: 355–359 (1982).
Blumenthal et al., J. Bacteriol. 164: 501–509, (1985).
Wayne et al. Gene 202: 83–88, (1997).
Kiss et al., Nucl. Acids Res. 13: 6403–6421, (1985).
Szomolanyi et al., Gene 10: 219–225, (1980).
Janulaitis et al., Gene 20: 197–204 (1982).
Kiss and Baldauf, Gene 21: 111–119, (1983).
Walder et al., J. Biol. Chem. 258: 1235–1241, (1983).
Fomenkov et al., Nucl. Acids Res. 22: 2399–2403, (1994).
Malone et al., J. Mol. Biol. 253: 618–632, (1995).
New England Biolabs' Catalog, 2000–01, p. 220.

*Primary Examiner*—Charles L. Patterson, Jr.
(74) *Attorney, Agent, or Firm*—Gregory D. Williams

(57) ABSTRACT

The present invention relates to recombinant DNA that encodes the BseRI restriction endonuclease as well as M.BseRI, expression of BseRI restriction endonuclease and M.BseRI in *E. coli* cells containing the recombinant DNA.

6 Claims, 11 Drawing Sheets

FIG. 2A

```
      ATGAAGGGAAATCAGATAATAGACAACTCAAATAACCTCTCATTAAATTCTAATGAATCG
  1   ---------+---------+---------+---------+---------+---------+   60
       M  K  G  N  Q  I  I  D  N  S  N  N  L  S  L  N  S  N  E  S
      TTGTTTAATTTATATTCTCAACCGCTACCAGCTTCAAGGAGCGGTGCTTTATACAATGCA
 61   ---------+---------+---------+---------+---------+---------+  120
       L  F  N  L  Y  S  Q  P  L  P  A  S  R  S  G  A  L  Y  N  A
      TTTTCTTATCCTACAAAGATATCTCCAGAATCTATTGCAGTTTTTATTGCTTCTCATACT
121   ---------+---------+---------+---------+---------+---------+  180
       F  S  Y  P  T  K  I  S  P  E  S  I  A  V  F  I  A  S  H  T
      AAACCAGGAGATGTTGTACTAGATACCTTTGGTGGAAGTGGTACAACTGGAATTGCAGCG
181   ---------+---------+---------+---------+---------+---------+  240
       K  P  G  D  V  V  L  D  T  F  G  G  S  G  T  T  G  I  A  A
      CATTTATGTGCTAACCCAACAAAAGAAGTTATTGATTTAGCTGAGCAACTTAAGGCACCA
241   ---------+---------+---------+---------+---------+---------+  300
       H  L  C  A  N  P  T  K  E  V  I  D  L  A  E  Q  L  K  A  P
      GTGGAATGGGGACCTAGAACTGCAATAATTTATGAGCTTAGTACGCTGGGATCTTTCGTT
301   ---------+---------+---------+---------+---------+---------+  360
       V  E  W  G  P  R  T  A  I  I  Y  E  L  S  T  L  G  S  F  V
      GGGCGTACAATAACAACTCAAACAGATTCTAAGGAATTTTTAAAAAGTGCAGAAGAACTT
361   ---------+---------+---------+---------+---------+---------+  420
       G  R  T  I  T  T  Q  T  D  S  K  E  F  L  K  S  A  E  E  L
      ATAAAGAAATGTGAACAGGAAGTTGGAAACATTTATAAAGCAAGAGATGATAAAGGGGAT
421   ---------+---------+---------+---------+---------+---------+  480
       I  K  K  C  E  Q  E  V  G  N  I  Y  K  A  R  D  D  K  G  D
      TTAGGAACAATTCGACACAGTATTTGGAGTGACGTTTTAAAGTGTTCAGATTGTAACAAA
481   ---------+---------+---------+---------+---------+---------+  540
       L  G  T  I  R  H  S  I  W  S  D  V  L  K  C  S  D  C  N  K
      GAAGTAGCATTTTGGGATGTGGCTGTTCAACAATCTCCTTTGAAAATATTGGATAAATTT
541   ---------+---------+---------+---------+---------+---------+  600
       E  V  A  F  W  D  V  A  V  Q  Q  S  P  L  K  I  L  D  K  F
      AAATGTCCTTCGTGTGGCTTTGAAGCTGGAATAAATCAAGTTGAGCGTGTTTTTGAACCT
601   ---------+---------+---------+---------+---------+---------+  660
       K  C  P  S  C  G  F  E  A  G  I  N  Q  V  E  R  V  F  E  P
      TATTTTGATGAATTGCTAGGAAAAGAACAAATAAGAAAAAAAAGAGTTCTTAAAAGAATA
661   ---------+---------+---------+---------+---------+---------+  720
       Y  F  D  E  L  L  G  K  E  Q  I  R  K  K  R  V  L  K  R  I
      TACGGACAGACTGGTAAGCGGAATTGGCAACGCCCTGCTAATGCAGAGGATGAAGATTTA
721   ---------+---------+---------+---------+---------+---------+  780
       Y  G  Q  T  G  K  R  N  W  Q  R  P  A  N  A  E  D  E  D  L
      ATTAAGAATATTGAAAGTATGCCTCTTCCGAAAGATATTCCACTTCAACAGaTTCCATGG
781   ---------+---------+---------+---------+---------+---------+  840
       I  K  N  I  E  S  M  P  L  P  K  D  I  P  L  Q  Q  I  P  W
      GGAGATTTATATAGAGCAGGATATCACAAGGGAATAACTCATGCCCATCATTTTTATACA
841   ---------+---------+---------+---------+---------+---------+  900
       G  D  L  Y  R  A  G  Y  H  K  G  I  T  H  A  H  H  F  Y  T
      ACAAGAAATTTAATAGTGATGGCAACACTGTGGGAAGGCATTAAATCGGCACCTGCGGAA
901   ---------+---------+---------+---------+---------+---------+  960
       T  R  N  L  I  V  M  A  T  L  W  F  G  I  K  S  A  P  A  E
      TTACAAGATGCCCTAAAATTATTAGTTCTAAGTTACAATTCTACACATTCTACATTGATG
961   ---------+---------+---------+---------+---------+---------+ 1020
       L  Q  D  A  L  K  L  L  V  L  S  Y  N  S  T  H  S  T  L  M
```

FIG. 2B

```
     ACCAGAGTAGTAGTGAAGTCGAACCAACCAGATTTTGTTTTAACTAGTGCTCAATCTGGG
1021 ------------------------------------------------------------+ 1080
      T  R  V  V  V  K  S  N  Q  P  D  F  V  L  T  S  A  Q  S  G
     GTTCTGTACATTAGTAGTTTACCTGTAGAAAAAAATTTATTTGAAGGCTTAAAGCGGAAA
1081 ------------------------------------------------------------+ 1140
      V  L  Y  I  S  S  L  P  V  E  K  N  L  F  E  G  L  K  R  K
     GCTAAAACAATTGGAAAAGCATTTGCTATTTTAGAAAATAGCGACAGTAATGTAACCGTA
1141 ------------------------------------------------------------+ 1200
      A  K  T  I  G  K  A  F  A  I  L  E  N  S  D  S  N  V  T  V
     GTTAACGGAACTAGTACAGATCTTGATATACCAGATAAATCTGTAGACTATGTTTTTACG
1201 ------------------------------------------------------------+ 1260
      V  N  G  T  S  T  D  L  D  I  P  D  K  S  V  D  Y  V  F  T
     GATCCTCCGTTTGGAGATTATATTCCTTATGCGGAACTAAATTTTCTTAACGAGGTATGG
1261 ------------------------------------------------------------+ 1320
      D  P  P  F  G  D  Y  I  P  Y  A  E  L  N  F  L  N  E  V  W
     CTAGGTAAAACAACTAATCGTACTAATGAAATTATTATTAGTCCAAAGCAGGAAAAATCG
1321 ------------------------------------------------------------+ 1380
      L  G  K  T  T  N  R  T  N  E  I  I  I  S  P  K  Q  E  K  S
     GTTACTACCTATGCGGAGTTGATGGCTGGTGTTTTTAAAGAGATTTCTCGAACATTAAAA
1381 ------------------------------------------------------------+ 1440
      V  T  T  Y  A  E  L  M  A  G  V  F  K  E  I  S  R  T  L  K
     AATGATGGTGCAGCTACGGTAGTGTTTCATTCTGCAAAAGCAGAAGTATGGAAATCATTA
1441 ------------------------------------------------------------+ 1500
      N  D  G  A  A  T  V  V  F  H  S  A  K  A  E  V  W  K  S  L
     CAAGACTCTTATAAACATGCAGGTTTAAAGGTAAAGTATTCAAGTGTGCTTGATAAGTTA
1501 ------------------------------------------------------------+ 1560
      Q  D  S  Y  K  H  A  G  L  K  V  K  Y  S  S  V  L  D  K  L
     CAGGGAAGTTTTAAACAAGTATCTAAAAGTGTTTCTGTTAAAGGAGATCCTCTCTTGTAT
1561 ------------------------------------------------------------+ 1620
      Q  G  S  F  K  Q  V  S  K  S  V  S  V  K  G  D  P  L  L  Y
     CTTACAAAAGAGGAACGTAATTCTGTCCTTGAACCTTCCCATATTGATATTGAAGCTACT
1621 ------------------------------------------------------------+ 1680
      L  T  K  E  E  R  N  S  V  L  E  P  S  H  I  D  I  E  A  T
     ATATCACAGCTACTTCAAGAAGCAATTGCTTCTAAAGATGATAAAGAACGTACAGTGGAA
1681 ------------------------------------------------------------+ 1740
      I  S  Q  L  L  Q  E  A  I  A  S  K  D  D  K  E  R  T  V  E
     AGAATTTATACTCGTTTTATATCGAAATTTTTAGAAAGTGGACAAGAGGTTCCTCTTGAT
1741 ------------------------------------------------------------+ 1800
      R  I  Y  T  R  F  I  S  K  F  L  E  S  G  Q  E  V  P  L  D
     GCAGCTGATTTTTATCGTAAAGTGAAACCATTGCTTAAAATAAGTGATTTTAGAAACGAA
1801 ------------------------------------------------------------+ 1860
      A  A  D  F  Y  R  K  V  K  P  L  L  K  I  S  D  F  R  N  E
     GTCCCAATTCCAAAAGATATAAAGATACAAATTAATCCAGAACGACAAAAAAGGTTGGGA
1861 ------------------------------------------------------------+ 1920
      V  P  I  P  K  D  I  K  I  Q  I  N  P  E  R  Q  K  R  L  G
     CAATATTTTACTAGTGGACCGTTAGCTGAGCTGCTAGCAACAATTGCAGAAGGAAGTACA
1921 ------------------------------------------------------------+ 1980
      Q  Y  F  T  S  G  P  L  A  E  L  L  A  T  I  A  E  G  S  T
     GCCTCTTCTGTAATTGATCCGATGTGTGGCCAAGGAGATATGCTTACAGCGGTTAATTCG
1981 ------------------------------------------------------------+ 2040
      A  S  S  V  I  D  P  M  C  G  Q  G  D  M  L  T  A  V  N  S
     ATTAATTCAAAAGCAAACCTTTCTGGCATAGACATTGATCCAATTGCTATGAATAAATGT
```

FIG. 2C

```
2041 ----------+----------+----------+----------+----------+----------+ 2100
     I  N  S  K  A  N  L  S  G  I  D  I  D  P  I  A  M  N  K  C
     ATTGATCGTTTAGGTAATCAAAAAAAATCTCTAGACTTAATAATTGGGAGTGCCTTCAGT
2101 ----------+----------+----------+----------+----------+----------+ 2160
     I  D  R  L  G  N  Q  K  K  S  L  D  L  I  I  G  S  A  F  S
     TGGAATACGATTAAGCAATTAAAATTGAAAAGTTTTGACCTTGTAATTACGAATCCTCCG
2161 ----------+----------+----------+----------+----------+----------+ 2220
     W  N  T  I  K  Q  L  K  L  K  S  F  D  L  V  I  T  N  P  P
     TATGTTAGGTATCAATCACTTTCTTCGAAGTTGGAAGGAGACGTGTTATTACCTGATTCA
2221 ----------+----------+----------+----------+----------+----------+ 2280
     Y  V  R  Y  Q  S  L  S  S  K  L  E  G  D  V  L  L  P  D  S
     GAAACAGTGAGAAATGATTTACTTGAGGTTGTATCTCAACTTGATCACTTAGAGCATAGA
2281 ----------+----------+----------+----------+----------+----------+ 2340
     E  T  V  R  N  D  L  L  E  V  V  S  Q  L  D  H  L  E  H  R
     GATAAAGAAGTGTTTAGAACAGTAATTAAGTCTTATTCTGGCTTATCTGATTTAGCGGTA
2341 ----------+----------+----------+----------+----------+----------+ 2400
     D  K  E  V  F  R  T  V  I  K  S  Y  S  G  L  S  D  L  A  V
     CCTTCGTGGATATTATGTGCAATGCTTACATCAGTTGGAGGACATTTAGCTATGGTGGTG
2401 ----------+----------+----------+----------+----------+----------+ 2460
     P  S  W  I  L  C  A  M  L  T  S  V  G  G  H  L  A  M  V  V
     CCTGAATCATGGTTAAATAGAGATTATGCCCACCCTATTCATTACTTGTTACTCAAGCTT
2461 ----------+----------+----------+----------+----------+----------+ 2520
     P  E  S  W  L  N  R  D  Y  A  H  P  I  H  Y  L  L  L  K  L
     TTCAAGATTAAATGGGTTGTTGAAGATGTCAATCGTACATGGTTTAAAGATGCGCAAGTA
2521 ----------+----------+----------+----------+----------+----------+ 2580
     F  K  I  K  W  V  V  E  D  V  N  R  T  W  F  K  D  A  Q  V
     AAGACAAATTTAGTTGTAGCTGAGAGAATTTCATATGTAGAAGATATTATAGAAAAATGT
2581 ----------+----------+----------+----------+----------+----------+ 2640
     K  T  N  L  V  V  A  E  R  I  S  Y  V  E  D  I  I  E  K  C
     CAAATAGAAAAGTATCTACATGTGGCTCTTCCAGAAATTTTAGCTGACTCATCTAGTATA
2641 ----------+----------+----------+----------+----------+----------+ 2700
     Q  I  E  K  Y  L  H  V  A  L  P  E  I  L  A  D  S  S  S  I
     GTTGGCGGTTTATTTCCGGGCTCAGTAACCCCAAACGAAGATTTTTATAATTTGTTAAAG
2701 ----------+----------+----------+----------+----------+----------+ 2760
     V  G  G  L  F  P  G  S  V  T  P  N  E  D  F  Y  N  L  L  K
     AGGGTAAAAGGTAACTCTGATTTAGAAATTATGAAGTTCCCAATAATGTATCGAAATATT
2761 ----------+----------+----------+----------+----------+----------+ 2820
     R  V  K  G  N  S  D  L  E  I  M  K  F  P  I  M  Y  R  N  I
     AAAACTAAATTAGATGATTTCATTGCTACTTCATTTAATTCAGAGTGGTTTAGAAGCTGT
2821 ----------+----------+----------+----------+----------+----------+ 2880
     K  T  K  L  D  D  F  I  A  T  S  F  N  S  E  W  F  R  S  C
     GAACCGAATCTTGTGAAACAAATTAAGAATCAAAGGCTAAAAGGCAAGAGCAGTACAGTT
2881 ----------+----------+----------+----------+----------+----------+ 2940
     E  P  N  L  V  K  Q  I  K  N  Q  R  L  K  G  K  S  S  T  V
     AAAATGCCACAACAGTTACTAGATGTTGTTCAGATTAGTAATATTGATTTTTGCTCAATT
2941 ----------+----------+----------+----------+----------+----------+ 3000
     K  M  P  Q  Q  L  L  D  V  V  Q  I  S  N  I  D  F  C  S  I
     GAAGACCTAGGATGGAAGGTTGGACAAGGCTTAAGAACAGGTGCTAATTCTTTCTTTTAC
3001 ----------+----------+----------+----------+----------+----------+ 3060
     E  D  L  G  W  K  V  G  Q  G  L  R  T  G  A  N  S  F  F  Y
     TGTGATGTTATAAATGAAACAGAAGAATACAGTACGGTGGTTACAAGCAAAAAGTTGGGG
3061 ----------+----------+----------+----------+----------+----------+ 3120
     C  D  V  I  N  E  T  E  E  Y  S  T  V  V  T  S  K  K  L  G
```

FIG. 2D

```
     TCAAGGACCTTTAATTTGCCTAAGGATGCATTATTGCCTGTTTTAAGAAAACAAAATGAA
3121 ------------+---------+---------+---------+---------+---------+ 3180
       S  R  T  F  N  L  P  K  D  A  L  L  P  V  L  R  K  Q  N  E
     ATTAAAGATAATTTTTTATTGCTTCAAAACCAGTTATATGGAAGAGTTCTTTTTTTAGAA
3181 ------------+---------+---------+---------+---------+---------+ 3240
       I  K  D  N  F  L  L  L  Q  N  Q  L  Y  G  R  V  L  F  L  E
     AATTATATTCATCCACAAGACTTGTCAAAAATTAGTGAGAGTTTAATATTACCTATAGAT
3241 ------------+---------+---------+---------+---------+---------+ 3300
       N  Y  I  H  P  Q  D  L  S  K  I  S  E  S  L  I  L  P  I  D
     ATTGGTCGAAAAGTCATGCCTTTAGAAATGCAGAATCTAATCGATTTGGCTACTGATATA
3301 ------------+---------+---------+---------+---------+---------+ 3360
       I  G  R  K  V  M  P  L  E  M  Q  N  L  I  D  L  A  T  D  I
     AATGTAGGGACAATGGAAAAGCCAAAATTTATACCTAGTTTATCTGCAGTTCGGACTAAT
3361 ------------+---------+---------+---------+---------+---------+ 3420
       N  V  G  T  M  E  K  P  K  F  I  P  S  L  S  A  V  R  T  N
     GTAACTAAGCAACAAGACGTCAATGCGAGATTTTGGTATATGCTTCCACGATTGACTGGT
3421 ------------+---------+---------+---------+---------+---------+ 3480
       V  T  K  Q  Q  D  V  N  A  R  F  W  Y  M  L  P  R  L  T  G
     AGACATAAATCAGAATTATTTATTCCTCGTATTAATAACTTGCACCCAAAAACTTTGTTG
3481 ------------+---------+---------+---------+---------+---------+ 3540
       R  H  K  S  E  L  F  I  P  R  I  N  N  L  H  P  K  T  L  L
     AATTCTAACAATACAGTTATTGATGCTAACTTCTCGACCTTGTGGGTGAATAAGGAAACA
3541 ------------+---------+---------+---------+---------+---------+ 3600
       N  S  N  N  T  V  I  D  A  N  F  S  T  L  W  V  N  K  E  T
     ATAGTAGATAAATATGCTATTTTAGCCTTATTCAACAGCACATGGGCTATAGCATTTATG
3601 ------------+---------+---------+---------+---------+---------+ 3660
       I  V  D  K  Y  A  I  L  A  L  F  N  S  T  W  A  I  A  F  M
     GAATTAACAGGAAGTGTTATGGGAGGCGGTGCATTAAAATTAGAAGCAACACATCTTAAG
3661 ------------+---------+---------+---------+---------+---------+ 3720
       E  L  T  G  S  V  M  G  G  G  A  L  K  L  E  A  T  H  L  K
     CGCCTGCCAATTCCCGCTCTTTTAGATGAGGGTTGGCAAAGGCTATCTCACCTAGGTAAA
3721 ------------+---------+---------+---------+---------+---------+ 3780
       R  L  P  I  P  A  L  L  D  E  G  W  Q  R  L  S  H  L  G  K
     GCTCTAATATATATGGAAGATGAACTCGAAACATTGAAACAAATAGACGATATAATTCTT
3781 ------------+---------+---------+---------+---------+---------+ 3840
       A  L  I  Y  M  E  D  E  L  E  T  L  K  Q  I  D  D  I  I  L
     AAAGCTATAACAGGGAAGAGCAACGTACTTCCTACCTTAGAGCTCTTAGAAAAAATTAAA
3841 ------------+---------+---------+---------+---------+---------+ 3900
       K  A  I  T  G  K  S  N  V  L  P  T  L  E  L  L  E  K  I  K
     ATCGAAAAGCTTTCTTTTAGAAATAAATAA
3901 ------------+---------+ 3930
       I  E  K  L  S  F  R  N  K  *
```

FIG. 3A

```
    ATGAACAATAGTGAAAAGCAAGTTGAGCTAGCTAGAGAGTGTATAATCGCTAGTTTGGGC
1   ------------------------------------------------------------  60
    M  N  N  S  E  K  Q  V  E  L  A  R  E  C  I  I  A  S  L  G
    TTAATTCGAGGGGGAAAAGTCGAGGACGTAATTCGCCATAGTTTTACTTCCTATTTGCGA
61  ------------------------------------------------------------  120
    L  I  R  G  G  K  V  E  D  V  I  R  H  S  F  T  S  Y  L  R
    ACTATGTTTCCTGATGAGCCAAGTTGGATTAAACAACATATAGAAGGTAGTGAGTCAGCA
121 ------------------------------------------------------------  180
    T  M  F  P  D  E  P  S  W  I  K  Q  H  I  E  G  S  E  S  A
    GTCAAGTTTTCTAAAGAAGGAAAGCTTCGGACTGGCTTTGTAGATAACTTGGTTGATCTT
181 ------------------------------------------------------------  240
    V  K  F  S  K  E  G  K  L  R  T  G  F  V  D  N  L  V  D  L
    ACAGCTATTGAATATGAATCAAACATCACCAATAAAACAAAGTTTGAGAATGGTTACGGT
241 ------------------------------------------------------------  300
    T  A  I  E  Y  E  S  N  I  T  N  K  T  K  F  E  N  G  Y  G
    CAGGTTAAAGATTATTGTGCCTCATTATTAAACAAAGGGTACGATTCTGAGCTAATATTG
301 ------------------------------------------------------------  360
    Q  V  K  D  Y  C  A  S  L  L  N  K  G  Y  D  S  E  L  I  L
    GGTGTATTGTCTGATACAGTTAGATGGAAAGCTTATAAGATAAAAACTATAGTTACTCCT
361 ------------------------------------------------------------  420
    G  V  L  S  D  T  V  R  W  K  A  Y  K  I  K  T  I  V  T  P
    GCCAATAGAAAGTTTGGTCGTGACGATATTGAGCTTGATGAGATTGAATCTATCGATTTG
421 ------------------------------------------------------------  480
    A  N  R  K  F  G  R  D  D  I  E  L  D  E  I  E  S  I  D  L
    TCATTAGCGGATAATTTAGCTGGAAAAAGGCTTATAGATTTTTTAAACACTTACCTTGGC
481 ------------------------------------------------------------  540
    S  L  A  D  N  L  A  G  K  R  L  I  D  F  L  N  T  Y  L  G
    CGATTAGGATCACGACCGTTGACTGCTTCCTCTCTAGCCAATGATTTAGGCTTTGATAGT
541 ------------------------------------------------------------  600
    R  L  G  S  R  P  L  T  A  S  S  L  A  N  D  L  G  F  D  S
    CACTTTTGTTCACGTCATATTTCTAGCCTTAGAGAGCTAGTAAATAATGCTTTTACTCAA
601 ------------------------------------------------------------  660
    H  F  C  S  R  H  I  S  S  L  R  E  L  V  N  N  A  F  T  Q
    AGACCAGAATATGGGGAAATGATTACTAATCTATGGTGTAGATTTGTGAGTTACCTAAGA
661 ------------------------------------------------------------  720
    R  P  E  Y  G  E  M  I  T  N  L  W  C  R  F  V  S  Y  L  R
    GATAAAAATTCTGTTGCAGAATTTGACAGAGAAATGTATTCAGATGAGTTATATATTTTA
721 ------------------------------------------------------------  780
    D  K  N  S  V  A  E  F  D  R  E  M  Y  S  D  E  L  Y  I  L
    ACCCTTGCAAAATTGGTATGTGCGAATATCATTGAAAATAGAGCACTACGGAGTGATAGA
781 ------------------------------------------------------------  840
    T  L  A  K  L  V  C  A  N  I  I  E  N  R  A  L  R  S  D  R
    GATGAAATATCAGCTATAATGCAAGGAGATTTTTTCAAGGTCAGAGGAATTATGAATCTA
841 ------------------------------------------------------------  900
    D  E  I  S  A  I  M  Q  G  D  F  F  K  V  R  G  I  M  N  L
    GTCGAATACGATTATTTTGGATGGCTTAACGAAGGTGAATTTCTTGAAAAAATAATACCT
901 ------------------------------------------------------------  960
    V  E  Y  D  Y  F  G  W  L  N  E  G  E  F  L  E  K  I  I  P
    GTGGCACAAGAAATGCAGGAAGATCTTATGGCTTATAATTTCTCAGCTCCGCCTGCGGAC
961 ------------------------------------------------------------  1020
```

FIG. 3B

```
            V  A  Q  E  M  Q  E  D  L  M  A  Y  N  F  S  A  P  P  A  D
         GATTTATTCGGTCAAATAATGGCACAGCTTGCTTCTCGTTCTCAAAGAATCTTACTTGGG
    1021 ---------+---------+---------+---------+---------+---------+ 1080
            D  L  F  G  Q  I  M  A  Q  L  A  S  R  S  Q  R  I  L  L  G
         CAGGAGTGGACACCGAAATGGTTAGCTAGTTCCATTGTCAAACAGGTTTTAGAAAAGTTA
    1081 ---------+---------+---------+---------+---------+---------+ 1140
            Q  E  W  T  P  K  W  L  A  S  S  I  V  K  Q  V  L  E  K  L
         CCGGTTGAGGAATTTCCTAAATTAGTTGATATGTGTTGTGGTTCTGGAGCACTTATAGTA
    1141 ---------+---------+---------+---------+---------+---------+ 1200
            P  V  E  E  F  P  K  L  V  D  M  C  C  G  S  G  A  L  I  V
         GAAGCAATAGAACAGTCAAAAGCAATGATAAAAAGAAACAAAATTACAAGTCAATCATCC
    1201 ---------+---------+---------+---------+---------+---------+ 1260
            E  A  I  E  Q  S  K  A  M  I  K  R  N  K  I  T  S  Q  S  S
         ATAGGTTTAGATCCAACTAACGGAAGTTCTGGAATGCTTATTAAATCGATAGAGGCAACA
    1261 ---------+---------+---------+---------+---------+---------+ 1320
            I  G  L  D  P  T  N  G  S  S  G  M  L  I  K  S  I  E  A  T
         CAATGTCTAAATGAAATAGAAATTGATCAAGCTGAAATTGAATTGCTTACCCAAGCAATC
    1321 ---------+---------+---------+---------+---------+---------+ 1380
            Q  C  L  N  E  I  E  I  D  Q  A  E  I  E  L  L  T  Q  A  I
         ACTGGTTTTGATATAGACCCTTTGGCAGTTATGTTATCCAAAATTAGCTGGTTACTTGCT
    1381 ---------+---------+---------+---------+---------+---------+ 1440
            T  G  F  D  I  D  P  L  A  V  M  L  S  K  I  S  W  L  L  A
         GCAAGGGATTGGTTAGAGCCGTTTGGAAGTTTTGAAGTAACTATTCCTGTTTATCATGCT
    1441 ---------+---------+---------+---------+---------+---------+ 1500
            A  R  D  W  L  E  P  F  G  S  F  E  V  T  I  P  V  Y  H  A
         GATTCATTGTTTGCTATTACACCATTATCAGATGTTATAGGTGAAGAAGAACAAGAAGAT
    1501 ---------+---------+---------+---------+---------+---------+ 1560
            D  S  L  F  A  I  T  P  L  S  D  V  I  G  E  E  E  Q  E  D
         TGTTACCAATTACAAATAGCAGAAGACTTAATTAAGCTCCCTAAATTTTTAATTTCACCT
    1561 ---------+---------+---------+---------+---------+---------+ 1620
            C  Y  Q  L  Q  I  A  E  D  L  I  K  L  P  K  F  L  I  S  P
         CAATTTCTAAATTATTTTGATACGTTAATAGATTTCGGCTATAATATTGCAATTACAATT
    1621 ---------+---------+---------+---------+---------+---------+ 1680
            Q  F  L  N  Y  F  D  T  L  I  D  F  G  Y  N  I  A  I  T  I
         GGAATGATTGAGGATAGAGAACTTGAGAGCTTTGTTAGTGCTACCTTAAATGATTCCGAG
    1681 ---------+---------+---------+---------+---------+---------+ 1740
            G  M  I  E  D  R  E  L  E  S  F  V  S  A  T  L  N  D  S  E
         CTCGAAGTCGACAGCGCAATGATTGTAAGTACAAAAAGGTTTCTATCTTCCTTTATATCA
    1741 ---------+---------+---------+---------+---------+---------+ 1800
            L  E  V  D  S  A  M  I  V  S  T  K  R  F  L  S  S  F  I  S
         ACAGTTAGCCGGCTTCATAGTGAGGGACGGAATGGAATATGGGCCTTTATTCTTCGTAAC
    1801 ---------+---------+---------+---------+---------+---------+ 1860
            T  V  S  R  L  H  S  E  G  R  N  G  I  W  A  F  I  L  R  N
         AGCTATCGACCAGGACTTGTGGCAGGACAGTTTAATGGCTTAGTATCAAATCCACCATGG
    1861 ---------+---------+---------+---------+---------+---------+ 1920
            S  Y  R  P  G  L  V  A  G  Q  F  N  G  L  V  S  N  P  P  W
         CTAGCTCTAAGCAAGATAGAGAATAATCCCTACCAACAGGTATTAAAAAAGAAAGCAGAG
    1921 ---------+---------+---------+---------+---------+---------+ 1980
            L  A  L  S  K  I  E  N  N  P  Y  Q  Q  V  L  K  K  K  A  E
         AGGTTTGGAATTAAACCGCCTGGTCCGGCATTTTTGCATATTGAAATGGCAACAACCTTT
```

FIG. 3C

```
1981 ---------+---------+---------+---------+---------+---------+ 2040
     R  F  G  I  K  P  P  G  P  A  F  L  H  I  E  M  A  T  T  F
     TTATTACATGCTGTCGATCGTTATCTTAAATCGGGGGCTGTAGTAGGGTGTATTACACCT
2041 ---------+---------+---------+---------+---------+---------+ 2100
     L  L  H  A  V  D  R  Y  L  K  S  G  A  V  V  G  C  I  T  P
     GAAACTGTCCTTAATGGATATAATCATGAACCTTTTAGACAATTGGCTTTTTCGAAGACC
2101 ---------+---------+---------+---------+---------+---------+ 2160
     E  T  V  L  N  G  Y  N  H  E  P  F  R  Q  L  A  F  S  K  T
     GCTAACCCTGTAAACTTTGAGCTTAACGAAATTTGGAAGCTTGAAGAGAATACATTTAAA
2161 ---------+---------+---------+---------+---------+---------+ 2220
     A  N  P  V  N  F  E  L  N  E  I  W  K  L  E  E  N  T  F  K
     AATAAGGGAATCGTTCTTTTTGGCACTAAGAGTAACAGCTCACCTGTACTTCCTAATCCA
2221 ---------+---------+---------+---------+---------+---------+ 2280
     N  K  G  I  V  L  F  G  T  K  S  N  S  S  P  V  L  P  N  P
     ATCCCAGGTGCTGTAGTAGGTAAAAATAGTTTATCTATAACAAGTTTTTTTATGAATACC
2281 ---------+---------+---------+---------+---------+---------+ 2340
     I  P  G  A  V  V  G  K  N  S  L  S  I  T  S  F  F  M  N  T
     CAAGGCAAAAGATCCGCTTTATCGGATAATCAAACTAACCGCGACAATAAGGCATCCTTA
2341 ---------+---------+---------+---------+---------+---------+ 2400
     Q  G  K  R  S  A  L  S  D  N  Q  T  N  R  D  N  K  A  S  L
     TCGCCTGGTTCTTTTAAGCAAGGGGCAGATATTATGCCTCGGAGACTACTGTTTCATGAA
2401 ---------+---------+---------+---------+---------+---------+ 2460
     S  P  G  S  F  K  Q  G  A  D  I  M  P  R  R  L  L  F  H  E
     ATAACACCTATAAAATCTGCAAAGGGAATACAACAGGTAAGTGTGAAGCCTATTGAGGTT
2461 ---------+---------+---------+---------+---------+---------+ 2520
     I  T  P  I  K  S  A  K  G  I  Q  Q  V  S  V  K  P  I  E  V
     GGAGTTAGTCCTTTATCATTCATAGTAAAAGATGCGAAAAAGTTATCTGATTTTAGGATA
2521 ---------+---------+---------+---------+---------+---------+ 2580
     G  V  S  P  L  S  F  I  V  K  D  A  K  K  L  S  D  F  R  I
     AATCCAACTGTGTTACCTAGTGATTTATTTTACGACGTTTTGACGTCTAACATGCTTACC
2581 ---------+---------+---------+---------+---------+---------+ 2640
     N  P  T  V  L  P  S  D  L  F  Y  D  V  L  T  S  N  M  L  T
     CCATTTAATATCGTTTCACCGGTTAAAGCACTATTACCAATACGTAGAGGAAGTAACGAT
2641 ---------+---------+---------+---------+---------+---------+ 2700
     P  F  N  I  V  S  P  V  K  A  L  L  P  I  R  R  G  S  N  D
     AAATGGGAACCATTAACAGAAGGTTCATTAATAGCTAAAGGTCAGAGAGTCAATTTAGCT
2701 ---------+---------+---------+---------+---------+---------+ 2760
     K  W  E  P  L  T  E  G  S  L  I  A  K  G  Q  R  V  N  L  A
     TTTAAACAGATATTTAGCGCTATGGGAAATAAAGCGGATATAAATACATTATGGAACCAA
2761 ---------+---------+---------+---------+---------+---------+ 2820
     F  K  Q  I  F  S  A  M  G  N  K  A  D  I  N  T  L  W  N  Q
     ATAAACACAAGAGGAAAGCTTGCTCAGCAGGTTATTCAACCTGGTGGATATTTACTGTTT
2821 ---------+---------+---------+---------+---------+---------+ 2880
     I  N  T  R  G  K  L  A  Q  Q  V  I  Q  P  G  G  Y  L  L  F
     ACTGGTACTAGTGGTGAAAAAGTATGCTCAGCTTTTTTAGATACTCAAAAGATAGACATT
2881 ---------+---------+---------+---------+---------+---------+ 2940
     T  G  T  S  G  E  K  V  C  S  A  F  L  D  T  Q  K  I  D  I
     GAGAGGCTTATAATTGACCAGACCCTAAACTGGGCTACAGTGGAGACTTTAGATGAAGCA
2941 ---------+---------+---------+---------+---------+---------+ 3000
```

FIG. 3D

```
              E  R  L  I  I  D  Q  T  L  N  W  A  T  V  E  T  L  D  E  A
         TGTTATATTACAGGCCTTTTCAATAGTGAAGCAATTAACCTTATGATAAAGGATTTTCAA
    3001 ---------+---------+---------+---------+---------+---------+ 3060
         CCAGAGGGTGCTTTTGGGGGACGTCATATTCATTCTCTTCCTTTCAGAGTGACACCACGG
          C  Y  I  T  G  L  F  N  S  E  A  I  N  L  M  I  K  D  F  Q
                 P  E  G  A  F  G  G  R  H  I  H  S  L  P  F  R  V  T  P  R
         CCAGAGGGTGCTTTTGGGGGACGTCATATTCATTCTCTTCCTTTCAGAGTGACACCACGG
    3061 ---------+---------+---------+---------+---------+---------+ 3120
         TTTGATTCAACGCAACCCGCTCATCAAGAAGTAGTAGAAAAAACTAAGTTTTTAATCATG

P  E  G  A  F  G  G  R  H  I  H  S  L  P  F  R  V  T  P  R
         TTTGATTCAACGCAACCCGCTCATCAAGAAGTAGTAGAAAAAACTAAGTTTTTAATCATG
    3121 ---------+---------+---------+---------+---------+---------+ 3180
         GAATTTCAAGGTTTAAAGCATTCTGATCCAACAATAGAAGAAAATTTACTTAATCCTAAT
          F  D  S  T  Q  P  A  H  Q  E  V  V  E  K  T  K  F  L  I  M
              E  F  Q  G  L  K  H  S  D  P  T  I  E  E  N  L  L  N  P  N
         GAATTTCAAGGTTTAAAGCATTCTGATCCAACAATAGAAGAAAATTTACTTAATCCTAAT
    3181 ---------+---------+---------+---------+---------+---------+ 3240
         TTTAGTACTCTTGCGAGAAGAAGGAAGTTGATTAAAGATTTAATTAAAAGCCTTCCTGGG
              F  S  T  L  A  R  R  R  K  L  I  K  D  L  I  K  S  L  P  G
         TTTAGTACTCTTGCGAGAAGAAGGAAGTTGATTAAAGATTTAATTAAAAGCCTTCCTGGG
    3241 ---------+---------+---------+---------+---------+---------+ 3300
         TATGCAGACTATGAGTTAGCGTGCCGTAATCTTTATGGAGTTTAA
    3301 ---------+---------+---------+---------+----- 3345
          Y  A  D  Y  E  L  A  C  R  N  L  Y  G  V  *
```

METHOD FOR CLONING AND EXPRESSION OF BSERI RESTRICTION ENDONUCLEASE AND BSERI METHYLASE IN E. COLI

BACKGROUND OF THE INVENTION

The present invention relates to recombinant DNA that encodes the BseRI restriction endonuclease (endonuclease) as well as BseRI methyltransferase (methylase), expression of BseRI endonuclease and methylase in E. coli cells containing the recombinant DNA.

BseRI endonuclease is found in the strain of Bacillus species R (CAMB2669) (New England Biolabs' strain collection). It recognizes the double-stranded DNA sequence 5'GAGGAG3' $N_{10}/N_8$ (SEQ ID NO:1) and cleaves the downstream sequence at $N_{10}$ of the top strand and $N_8$ of the bottom strand, generating a 2-base 3' overhang (N=A, C, G, or T). BseRI methylase (M.BseRI) is also found in the same strain. It recognizes the double-stranded DNA sequence 5'GAGGAG3' (SEQ ID NO:1) and presumably modifies the N6 adenine on the top strand and the N4 cytosine on the bottom strand of 5'CTCCTC3' (SEQ ID NO:2).

Type II restriction endonucleases are a class of enzymes that occur naturally in bacteria and in some viruses. When they are purified away from other bacterial/viral proteins, restriction endonucleases can be used in the laboratory to cleave DNA molecules into small fragments for molecular cloning and gene characterization.

Restriction endonucleases recognize and bind particular sequences of nucleotides (the 'recognition sequence') along the DNA molecules. Once bound, they cleave the molecule within (e.g. BamHI), to one side of (e.g. SapI), or to both sides (e.g. TspRI) of the recognition sequence. Different restriction endonucleases have affinity for different recognition sequences. Over two hundred and eleven restriction endonucleases with unique specificities have been identified among the many hundreds of bacterial species that have been examined to date (Roberts and Macelis, Nucl. Acids Res. 27:312–313, (1999)).

Restriction endonucleases typically are named according to the bacteria from which they are discovered. Thus, the species *Deinococcus radiophilus* for example, produces three different restriction endonucleases, named DraI, DraII and DraIII. These enzymes recognize and cleave the sequences 5'TTT/AAA3' (SEQ ID NO:3), 5'PuG/GNCCPy3' (SEQ ID NO:4) and 5'CACNNN/GTG3' (SEQ ID NO:5) respectively. *Escherichia coli* RY13, on the other hand, produces only one enzyme, EcoRI, which recognizes the sequence 5'G/AATTC3' (SEQ ID NO:6).

A second component of bacterial/viral restriction-modification (R-M) systems are the methylase. These enzymes co-exist with restriction endonucleases and they provide the means by which bacteria are able to protect their own DNA and distinguish it from foreign DNA. Modification methylases recognize and bind to the same recognition sequence as the corresponding restriction endonuclease, but instead of cleaving the DNA, they chemically modify one particular nucleotide within the sequence by the addition of a methyl group (C5 methyl cytosine, N4 methyl cytosine, or N6 methyl adenine). Following methylation, the recognition sequence is no longer cleaved by the cognate restriction endonuclease. The DNA of a bacterial cell is always fully modified by the activity of its modification methylase. It is therefore completely insensitive to the presence of the endogenous restriction endonuclease. Only unmodified, and therefore identifiably foreign DNA, is sensitive to restriction endonuclease recognition and cleavage. During and after DNA replication, usually the hemi-methylated DNA (DNA methylated on one strand) is also resistant to the cognate restriction digestion.

With the advancement of recombinant DNA technology, it is now possible to clone genes and overproduce the enzymes in large quantities. The key to isolating clones of restriction endonuclease genes is to develop an efficient method to identify such clones within genomic DNA libraries, i.e. populations of clones derived by 'shotgun' procedures, when they occur at frequencies as low as $10^{-3}$ to $10^{-4}$. Preferably, the method should be selective, such that the unwanted clones with non-methylase inserts are destroyed while the desirable rare clones survive.

A large number of type II restriction-modification systems have been cloned. The first cloning method used bacteriophage infection as a means of identifying or selecting restriction endonuclease clones (EcoRII: Kosykh et al., Mol. Gen. Genet. 178:717–719, (1980); HhaII: Mann et al., Gene 3:97–112, (1978); PstI: Walder et al., Proc. Nat. Acad. Sci. 78:1503–1507, (1981)). Since the expression of restriction-modification systems in bacteria enables them to resist infection by bacteriophages, cells that carry cloned restriction-modification genes can, in principle, be selectively isolated as survivors from genomic DNA libraries that have been exposed to phage. However, this method has been found to have only a limited success rate. Specifically, it has been found that cloned restriction-modification genes do not always confer sufficient phage resistance to achieve selective survival.

Another cloning approach involves transferring systems initially characterized as plasmid-borne into E. coli cloning vectors (EcoRV: Bougueleret et al., Nucl. Acids. Res. 12:3659–3676, (1984); PaeR7: Gingeras and Brooks, Proc. Natl. Acad. Sci. USA 80:402–406, (1983); Theriault and Roy, Gene 19:355–359 (1982); PvuII: Blumenthal et al., J. Bacteriol. 164:501–509, (1985); Tsp45I: Wayne et al. Gene 202:83–88, (1997)).

A third approach is to select for active expression of methylase genes (methylase selection) (U.S. Pat. No. 5,200,333 and BsuRI: Kiss et al., Nucl. Acids. Res. 13:6403–6421, (1985)). Since restriction-modification genes are often closely linked together, both genes can often be cloned simultaneously. This selection does not always yield a complete restriction system however, but instead yields only the methylase gene (BspRI: Szomolanyi et al., Gene 10:219–225, (1980); BcnI: Janulaitis et al., Gene 20:197–204 (1982); BsuRI: Kiss and Baldauf, Gene 21:111–119, (1983); and MspI: Walder et al., J. Biol. Chem. 258: 1235–1241, (1983)).

A more recent method, the "endo-blue method", has been described for direct cloning of thermostable restriction endonuclease genes into E. coli based on the indicator strain of E. coli containing the dinD::lacZ fusion (U.S. Pat. No. 5,498,535 (1996); Fomenkov et al., Nucl. Acids Res. 22:2399–2403, (1994)). This method utilizes the E. coli SOS response signals following DNA damage caused by restriction endonucleases or non-specific nucleases. A number of thermostable nuclease genes (TaqI, Tth111I, BsoBI, Tf nuclease) have been cloned by this method (U.S. Pat. No. 5,498,535). The disadvantage of this method is that some positive blue clones containing a restriction endonuclease gene are difficult to culture due to the lack of the cognate methylase gene.

There are three major groups of DNA methyltransferases based on the position and the base that is modified (C5 cytosine methylases, N4 cytosine methylases, and N6 adenine methylases). N4 cytosine and N6 adenine methylases are amino-methyltransferases (Malone et al. J. Mol. Biol. 253:618–632, (1995)). When a restriction site on DNA is modified (methylated) by the methylase, it is resistant to digestion by the cognate restriction endonuclease. Sometimes methylation by a non-cognate methylase can also confer the DNA site resistant to restriction digestion. For example, Dcm methylase modification of 5'CCWGG3' (SEQ ID NO:7) (W=A or T) can also make the DNA resistant to PspGI restriction digestion. Another example is that CpM methylase can modify the CG dinucloetide and make the NotI site (5'GCGGCCGC3' (SEQ ID NO:8)) refractory to NotI digestion (New England Biolabs' Catalog, 2000-01, page 220). Therefore methylases can be used as a tool to modify certain DNA sequences and make them uncleavable by restriction enzymes.

Because purified restriction endonucleases and modification methylases are useful tools for creating recombinant molecules in the laboratory, there is a strong commercial interest to obtain bacterial strains through recombinant DNA techniques that produce large quantities of restriction enzymes. Such over-expression strains should also simplify the task of enzyme purification.

SUMMARY OF THE INVENTION

The present invention relates to a method for cloning the BseRI restriction endonuclease from Bacillus species R into E. coli by direct PCR and inverse PCR amplification from genomic DNA.

It proved difficult to clone bseRIM gene by the conventional methylase selection method. At first, Sau3AI partial genomic DNA library, AatII, BamHI, and PstI complete genomic DNA libraries were constructed. After BseRI challenge, no true methylase positive clones were identified among the surviving transformants. Since the conventional methylase selection did not yield any positive clones, efforts were made to purify the native BseRI endonuclease.

BseRI endonuclease was purified from the native strain Bacillus cell extract by chromatography through Heparin hyper D, Source Q, Heparin tsk columns and gel filtration column Superdex 75. Two major proteins were identified on SDS-PAGE, one at ~55 kDa and the other at ~120 kDa. Both proteins were subjected to protein sequencing to obtain the N-terminus amino acid sequence. Amino acid sequence comparison with proteins in GenBank indicated that the ~55 kDa protein has high homology to Basillus Glutaminyl tRNA sythetase. Therefore, this protein was ruled out as the BseRI endonuclease. The N-terminal amino acid sequence of the ~120 kDa protein was sequenced and the sequence has no significant homology to proteins in GenBank. It was concluded that the ~120 kDa protein is most likely the BseRI endonuclease.

A protein at ~46 kDa was also identified in the production preparations of BseRI endonuclease (lot 8, 9, and 12). This protein was also sequenced, which generated a similar N-terminus amino acid sequence to the ~120 kDa. The ~46 kDa protein might be a protease degraded fragment of the ~120 kDa protein. Degenerate primers were synthesized based on the amino acid sequence. The 92-bp coding DNA was amplified by PCR using degenerate primers and cloned into a pUC-derivative and sequenced. The predicted amino acid sequence from the DNA sequence matched very well the actual amino acid sequence derived from the BseRI protein.

Inverse PCR and DNA sequencing were performed to obtain the remaining part of the bseRIR gene. After five round of inverse PCR amplifications and DNA sequencing the entire bseRIR endonuclease gene was sequenced and found to be 3345 bp, encoding a fusion protein with a restriction domain, a conserved methylase domain, and a specificity domain (R-M-S).

Because R-M genes in a particular R-M system are usually located in close proximity, efforts were made to identify the adjacent DNA sequences. After four rounds of inverse PCR amplifications, a large ORF of 3930 bp was found upstream of bseRIR gene. This large ORF encodes two amino-methylases (a N4 cytosine methylase and a N6 adenine methylase) that fused together to form BseRI methylase.

A pre-modified expression host ER2566 [pACYC-BseRIM] was constructed. The bseRIR gene was amplified by PCR from genomic DNA and cloned into a T7 expression vector pAII17. The expression strain was ER2566 [pACYC-BseRIM, pAII17-BseRIR]. An induced BseRI endonuclease protein band of approximately 120–125 kDa was detected in the IPTG-induced cell extract, but absent in the non-induced extract. The cell extract was confirmed to display recombinant BseRI endonuclease activity on λDNA.

BRIEF DESCRIPTION OF THE DRAWINGS

FIG. 2. BseRI methylase gene sequence (SEQ ID NO:9) (bseRIM, 3930 bp) and the encoded amino acid sequence (SEQ ID NO:10).

FIG. 3. BseRI endonuclease gene sequence (SEQ ID NO:11) (bseRIR, 3345 bp) and the encoded amino acid sequence (SEQ ID NO:12).

DETAILED DESCRIPTION OF THE INVENTION

Figure 1:
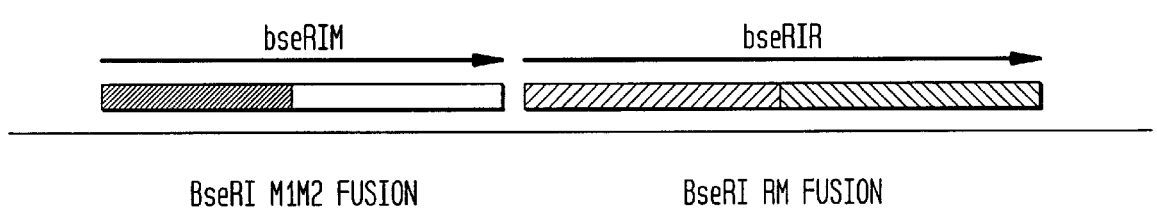
FIG. 1. Gene organization of BseRI R-M system. bseRIR, BseRI restriction endonuclease gene; BseRI endonuclease is a fusion of restriction and methylase (R-M-S). bseRIM, BseRI methylase gene; BseRI methylase is a fusion of two amino-methylases.

It was extremely difficult to clone bseRIM gene using the conventional methylase selection method. Sau3AI partial, AatII, BamHI, and PstI complete genomic DNA libraries were constructed and the methylase selection method was attempted to clone bseRIM gene. After intensive screening of these libraries following BseRI challenge, no true methylase positive clones were identified. It's possible that the BseRI methylase expressed poorly in E. coli in the native DNA context or the methylase gene may have been cleaved during library construction. Since the conventional methylase selection did not yield any positive clones, efforts were directed to purify the native BseRI endonuclease to obtain the N-terminus amino acid sequence. The goal was to use the N-terminal amino acid sequence to design primers in order to amplify the coding sequence directly from genomic DNA. This approach proved to be successful in cloning of BseRI R-M genes.

The method described herein by which the BseRI methylase gene and the BseRI restriction endonuclease genes are preferably cloned and expressed in *E. coli* using the following steps:

1. Purification of BseRI Endonuclease from the Native Strain

BseRI restriction endonuclease was purified from the native strain Bacillus species R cells by chromatography through Heparin hyper D, Source Q, Heparin tsk columns and gel filtration column Superdex 75. The active fractions were pooled and analyzed on an SDS-PAG gel. Two major proteins bands were identified, one at 55 kDa and the other at ~120 kDa. Both proteins were subjected to protein sequencing to obtain the N-terminus amino acid sequence.

2. Amino Acid Sequence Analysis of BseRI Endonuclease

The purified proteins were electro-blotted to a membrane. The membrane was then stained and the 55 kDa and ~120 kDa bands were excised and subjected to sequential degradation in an automated sequencer. The N-terminal amino acid sequence of the 55 kDa protein was compared to all the known proteins in GenBank using the computer program BlastP. The sequence comparison indicated that this protein has high homology to Bacillus Glutaminyl tRNA sythetase. It was concluded that this protein is not the BseRI endonuclease protein. The N-terminal amino acid sequence of the ~120 kDa protein was sequenced and contains the following N-terminus amino acid sequence:

MNNSEKQVELARE C/S IIASLGLIRGGKVED-VIRHXF (C/S=C or S, uncertain amino acid calling, X=unknown amino acid) (SEQ ID NO:13).

This sequence does not have any significant homology to any proteins in GenBank. It was concluded that the ~120 kDa protein is most likely the BseRI endonuclease.

A protein band at ~46 kDa was also found in production preparations of BseRI endonuclease (NEB lot 8, 9, and 12). This protein band was also subjected N-terminus amino acid sequencing, giving rise to a similar sequence to the 120 kDa. It was concluded that the ~46 kDa protein might be a protease degraded fragment of the ~120 kDa protein. Degenerate primers were synthesized to amplify the coding sequence directly from genomic DNA. It is critically important to make two degenerate forward primers because of the Ser codon, one with agy codon and the other with tcn codon. PCR with primer carrying agy codon worked, but PCR with primer carrying tcn codon failed.

3. Amplification of N-terminus Coding Sequence by PCR

The 92-bp coding DNA fragment was amplified by PCR using degenerate primers and cloned into a pUC-derivative and sequenced. The predicted amino acid sequence from the DNA sequence matches very well the actual amino acid sequence derived from the BseRI protein. The predicted amino acid sequence is shown below.

MNNSEKQVELARECIIASLGLIRG-GKVEDVIRHSFTS (SEQ ID NO:14)

4. Inverse PCR Amplification of bseRI Endonuclease Gene

After five round of inverse PCR amplifications and DNA sequencing the entire bseRIR endonuclease gene was sequenced and found to be 3345 bp, encoding a protein with 1114 amino acid with predicted molecular mass of 125 kDa.

5. Inverse PCR Amplification of bseRIM Gene

Because R-M genes in a particular R-M system are usually located in close proximity, efforts were made to identify the adjacent DNA sequences. After four rounds of inverse PCR amplifications, a start codon was found for the large open reading frame of 3930 bp. This large ORF encodes two amino-methylases (a N4 cytosine methylase and a N6 adenine methylasse) that fused together to form BseRI methylase. It is one of the largest type II methylases.

6. Expression of BseRIM Gene in *E. coli*

The BseRIM gene was amplified by PCR from genomic DNA. After DNA purification and restriction with SphI, the resulting DNA was cloned into pACYC184. Ten plasmid isolates demonstrated resistance to BseRI digestion, indicating the 2 BseRI sites in the vector had been fully modified by BseRI methylase. The resistant plasmid was used to transform ER2566 to generate the premodified expression host ER2566 [pACYC-BseRIM].

7. Expression of BseRI Endonuclease in *E. coli*.

Figure 4:
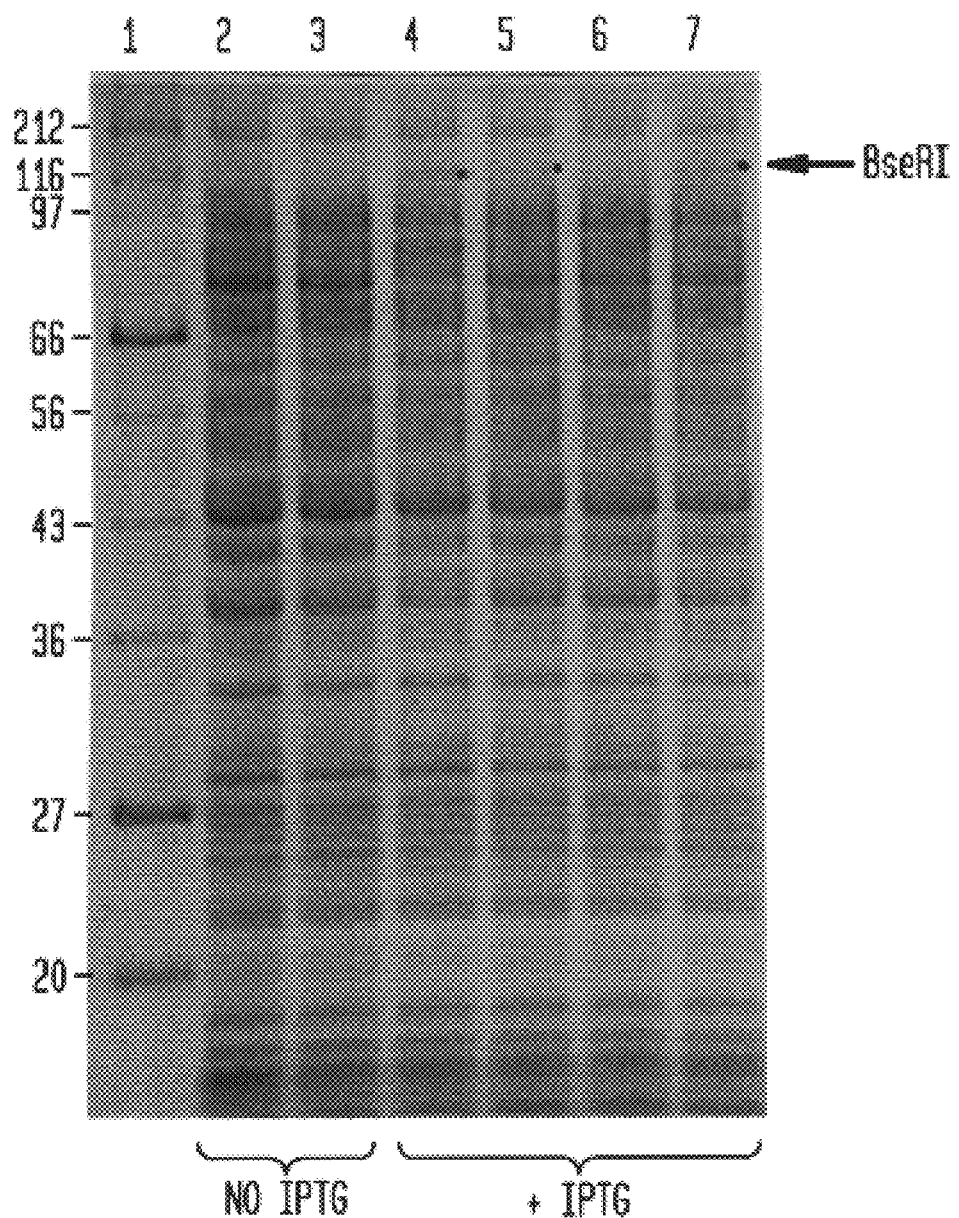
FIG. 4. Protein expression profiles of BseRI-producing clones on SDS-PAG gel. Lane 1, protein size marker; lane 2 and 3, non-induced cell extract (negative control); lanes 4, 5, 7, BseRI-positive, IPTG-induced cell extract; lane 6, BseRI-negative, IPTG-induced cell extract.
Figure 5:
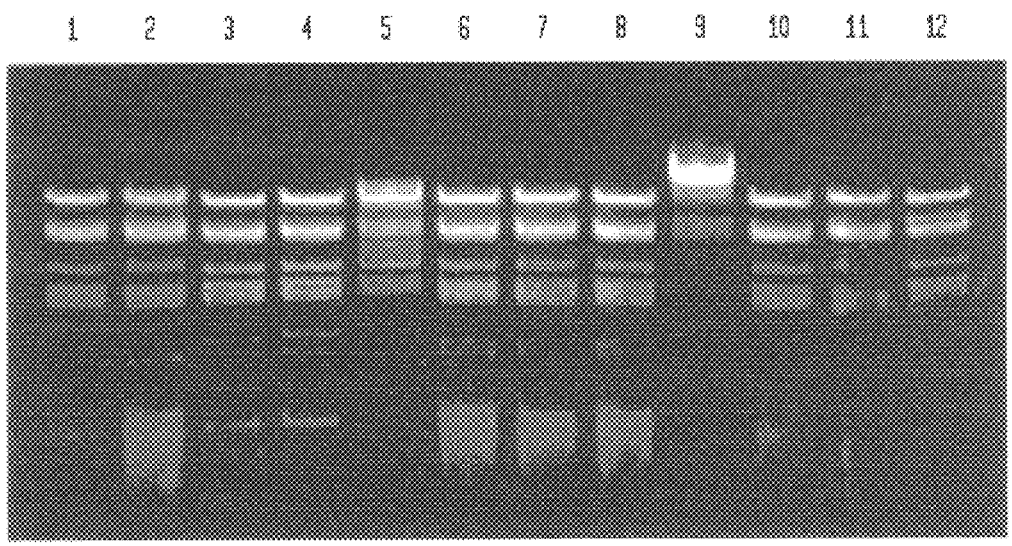
FIG. 5. Recombinant BseRI endonuclease activity in cell extract. Lanes 1–11, λ DNA digested with cell extracts containing recombinant BseRI endonuclease. Lanes 1–5, cell extract prepared from 500 ml IPTG-induced cell culture; lanes 6–11, cell extract prepared from 10 ml IPTG-induced cell culture. Lanes 1 and 2, λ DNA incubated with 1 and 2 µl cell extract, respectively; lanes 3, 4, and 5, λ DNA incubated with 2 µl of 1:10, 1:20, and 1:40 diluted extract. Lanes 6–11, λ DNA incubated with 2 µl cell extract. lane 12, λ DNA digested with purified native BseRI.

The bseRIR gene was amplified by PCR from genomic DNA using Vent DNA polymerase and cloned into a T7 expression vector pAII17. The expression strain was ER2566 [pACYC-BseRIM, pAII17-BseRIR]. IPTG-induced cell extract was prepared. The protein expression profiles of the induced and non-induced cell extracts were shown in FIG. 4. An induced protein band of approximately 125 kDa was detected in the IPTG-induced cell extract, but absent in the non-induced. One of the clones that displayed high BseRI activity in cell extract was shown in FIG. 5.

The present invention is further illustrated by the following Example. This Example is provided to aid in the understanding of the invention and is not construed as a limitation thereof.

The references cited above and below are herein incorporated by reference.

EXAMPLE 1

Cloning of BseRI Restriction-modification System in *E. coli*

1. Preparation of Genomic DNA

Genomic DNA was prepared from Bacillus species R (New England Biolabs collection) by the standard procedure consisting of the following steps:

(a) Cell lysis by addition of lysozyme (2 mg/ml final), sucrose (1% final), and 50 mM Tris-HCl, pH 8.0.

(b) Further cell lysis by addition of SDS at a final concentration of 0.1%.

(c) Further cell lysis by addition of 1% Triton X-100, 62 mM EDTA, 50 mM Tris-HCl, pH 8.0.

(d) Removal of proteins by phenol-$CHCl_3$ extraction of DNA 3 times (equal volume) and $CHCl_3$ extraction once.

(e) DNA dialysis in 4 liters of TE buffer, change 3 times.

(f) RNase A treatment to remove RNA and genomic DNA precipitation in 95% ethanol, centrifuged, washed, dried and resuspended in TE buffer.

2. Restriction Digestion of Genomic DNA and Construction of Genomic DNA Library

Restriction enzyme Sau3AI was diluted by 2-fold serial dilutions. Five to ten μg genomic DNA was digested partially with Sau3AI. The Sau3AI digested genomic DNA was ligated to BamHI digested and CIP treated pRRS vector that contained two BseRI sites. The Bacillus species R genomic DNA was also digested completely with AatII, BamHI, and PstI and ligated to pRRS-2BseRI with compatible ends. The ligated DNA was used to transform a DNaseI minus *E. coli* RR1 competent cells (ER2502) by electroporation. Approximately 36,000 AP$^R$ transformants were obtained for the Sau3AI library and ~6,000 AP$^R$ transformants were found in the AatII, BamHI and PstI libraries. The AatII, BamHI, PstI, and Sau3AI libraries were amplified in 1 liter LB+Ap overnight, respectively. Plasmid DNA was prepared by Qiagen Maxi-prep columns and challenged with BseRI overnight. The BseRI-digested DNA was used to transform ER2502 competent cells. Plasmid DNA was prepared from 1.5 ml cell cultures inoculated from the transformants and screened for resistance to BseRI digestion. Thirty-six plasmid mini-preparations were made for each libarary, but no true resistant clones were ever detected. It was concluded that either the BseRI methylase expressed poorly in *E. coli* or the methylase gene may have been cleaved during library construction. Since the conventional methylase selection did not yield any positive clones, efforts were made to purify the native BseRI endonuclease to obtain the N-terminus amino acid sequence.

3. Purification of BseRI Endonuclease from the Native Strain

One hundred g of Bacillus species R cells were resuspended in 400 ml of sonication buffer and sonicated for 1 min×20 times at 4° C. The clarified supernatant was loaded onto a 70 ml Heparin hyper D column. The column was washed extensively with 140 ml of a low salt buffer A (10 mM KPO$_4$, pH 7.0, 1 mM DTT, 0.1 mM EDTA). Proteins were eluted by applying a salt gradient of 0 to 1.5 M NaCl in buffer A to the column. Eluted fractions were assayed for BseRI activity on λ DNA and fractions 17–21 with high BseRI activity were pooled and dialyzed twice for 3 h in buffer B (50 mM NaCl, 10 mM Tris-HCl, pH 8.0, 1 mM DTT, 0.1 mM EDTA).

The BseRI protein was further purified by loading onto a 20 ml Source Q column. After washing with 40 ml of low salt buffer B, a 300 ml salt gradient of 50 mM–1 M in buffer B was applied to the column. BseRI activity in each fraction was identified by assaying activity on lambda DNA. Fractions 19 and 20 were collected and diluted to about 60 mM NaCl in Tris-HCl buffer.

The protein was applied to a 10 ml Heparin tsk column and after washing with 20 ml of low salt buffer C (10 mM Tris-HCl, 1 mM DTT, 0.1 mM EDTA) the protein was eluted with 150 ml 0–1.5 M salt gradient in buffer C. The BseRI fractions were pooled, diluted and applied to a 10 ml Source Q column and eluted with 150 ml 0–1 M salt gradient. The activity fractions were again identified and pooled and applied to a gel filtration column Superdex 75 (Hi load 26/60) in buffer D (0.5 M NaCl, 20 mM Tris-HCl, pH 8.0, 1 mM DTT, 0.1 mM EDTA). The active fractions 38–40 were pooled and analyzed on an SDS-PAG gel. Two major protein bands were identified, one at 55 kDa and the other at ~120 kDa. Both proteins were subjected to protein sequencing to obtain the N-terminus amino acid sequence.

4. Amino Acid Sequence Analysis of BseRI Endonuclease

The purified proteins were subjected to electrophoresis and electro-blotted to a membrane. The membrane was then stained with Commassie blue R-250 and the 55 kDa and ~120 kDa bands were excised and subjected to sequential degradation in an automated sequencer ABI model 470A. The 55 kDa protein contained the following N-terminal amino acid sequence:

(M)NEVRVRYAPSPTGH (SEQ ID NO:15)

This amino acid sequence was compared to all the known proteins in GenBank using the computer program BlastP. The sequence comparison indicated that this protein has high homology to Basillus Glutaminyl tRNA sythetase. It was concluded that this protein is not the BseRI endonuclease protein.

The ~120 kDa protein was sequenced and contains the following N-terminus amino acid sequence:

MNNSEKQVELARE C/S IIASLGLIRGGKVED-VIRHXF (SEQ ID NO:16) (C/S=C or S, uncertain amino acid calling, X=unknown amino acid).

A protein band at ~46 kDa was also found in production preparations of BseRI endonuclease (lot 8, 9, and 12). This protein band was also subjected N-terminus amino acid sequencing, giving rise to the following amino acid sequence:

MNN S/G EKQVELARE C/S IIASLGLIRGGKVED-VIRHSFTS (SEQ ID NO:17) (S/G=S OR G, C/S=C or S).

The N-terminal sequences of the ~46 kDa and ~120 kDa proteins matched each other. It was concluded that the ~46 kDa protein might be a protease degraded fragment of the ~120 kDa protein. When this amino acid sequence was compared to all proteins in Genbank, no significant homology was detected to known proteins. It was concluded that the ~120 kDa protein (or its ~46 kDa derivative) was the bona fide BseRI protein. Degenerate primers were synthesized to amplify the coding sequence directly from genomic DNA.

5. Amplification of N-terminus Coding Sequence by PCR

Two forward primers were made with the following sequence:

DNA 5'atg aay aay agy gar aar ca 3' (202-138) (SEQ ID NO:18)

DNA 5'atg aay aay tcn gar aar ca 3' (202-139) (SEQ ID NO:19)

Protein M N N S E K Q (SEQ ID NO:20)

The reverse primer has the following sequence:

DNA 5' atn acr tcy tcn acy tt 3' (202-140) (SEQ ID NO:21)

Protein I V D E V K (reverse of KVEDVI) (SEQ ID NO:22)

First set of PCR was set up using primers 202-138 and 202-140 and second set of PCR was set up with primers 202-139 and 202-140. PCR conditions were 95° C. 30 sec, 50° C. 1 min, 72° C. 30 sec, for 35 cycles using Taq DNA polymerase (10 μl genomic DNA at 0.1 μg, 2 μl of each primer at 0.12 μg/μl, 5.4 μl DNTP at 5 mM, 10 μl of 10× buffer, 70 μl sdH$_2$O, 1 μl Taq DNA polymerase at 5 u/μl). PCR product was found in the first set of PCR with primers 202-138 (with Ser codon agy) and 202-140. NO PCR product was detected in PCR with primers 202-139 (with Ser codon tcn) and 202-140. The PCR reaction was repeated to obtain more DNA, which was then gel-purified through a low-melting agarose gel. The 92-bp fragment was ligated to a pUC-derivative and transformed into *E. coli*. After screening 36 plasmid mini-preparations, one clone was found to contain the desired insert. The insert of this clone was sequenced using pUC universal primers and the coding sequence was found to encode the correct amino acid sequence derived from protein sequencing of the purified native BseRI endonuclease. The predicted amino acid sequence from the DNA sequence matches very well the actual amino acid sequence derived from the BseRI protein. The predicted amino acid sequence is shown below.

M N N S E K Q V E L A R E C I I A S L G L I R G-GKVEDVIRHSFTS (SEQ ID NO:23)

6. Inverse PCR Amplification of bseRI Endonuclease Gene

Two primers were synthesized with the following sequence:
5' gattatacactctctagctagctc 3' (226-18) (SEQ ID NO:24)
5' gctagtttgggcttaattcgaggggg 3' (226-19) (SEQ ID NO:25)

The genomic DNA was digested with AatII, ApoI, BsaWI, BspHI, BstUI, HhaI, HinP1I, HaeII, NspI, Sau3AI, Sau96I, and TfiI, respectively. The digested DNA was purified through a Qiagen spin column. Self-ligation was set up at a low DNA concentration at 2 μg/ml overnight at 16° C. T4 DNA ligase was inactivated at 65° C. for 30 min and 20 μl of the ligated product was used as the template for inverse PCR. PCR conditions were 95° C. 30 sec, 55° C. 30 sec, 72° C. 30 sec for 30 cycles. A 1.1 kb inverse PCR product was found in ApoI template. It was purified from a low-melting agarose gel and sequenced with primers 226-18 and 226-19. 1140 bp of DNA was derived from the first round of inverse PCR in which 730 bp DNA was the BseRI endonuclease coding sequence.

A second set of inverse PCR primers were made with the following sequences:
5' atttgtgagttacctaagagataa 3' (228-24) (SEQ ID NO:26)
5' ctacaccatagattagtaatcatt 3' (228-25) (SEQ ID NO:27)

The genomic DNA was digested with AflII, AvrII, ClaI, DraI, HaeII, HincII, NheI, NspI, NlaIII, SacI, StyI, and SspI, respectively. The digested DNA was purified through Qiagen spin columns. Self-ligation was set up at a low DNA concentration at 2 μg/ml overnight at 16° C. T4 DNA ligase was inactivated at 65° C. for 30 min and 20 μl of the ligated product was used as the template for inverse PCR. PCR conditions were 95° C. 30 sec, 55° C. 30 sec, 72° C. 2 min for 36 cycles. PCR products of 1900 bp, 1500 bp, 1850 bp, 1800 bp, and 1800 bp were found in ClaI, DraI, NheI, SacI, and NlaIII templates. The PCR products were purified from a low-melting agarose gel and sequenced with primers 228-24 and 228-25 and new sequence primers. The newly derived bseRIR gene sequence was combined with the existing sequence and the combined sequence was about 1345 bp and a stop codon had not been detected.

A third set of inverse PCR primers was synthesized with following sequences:
5' tctaaatgaaatagaaattg 3' (228-130) (SEQ ID NO:28)
5' cattgtgttgcctctatcgat 3' (228-129) (SEQ ID NO:29)

The genomic DNA was digested with AflII, AvrII, BglII, BstYI, HaeII, HincII, and SspI, respectively. The digested DNA was purified through Qiagen spin columns. Self-ligation was set up at a low DNA concentration at 2 μg/ml overnight at 16° C. T4 DNA ligase was inactivated at 65° C. for 30 min and 20 μl of the ligated product was used as the template for inverse PCR. PCR conditions were 95° C. 30 sec, 55° C. 30 sec, 72° C. 1 min for 35 cycles. PCR products of 2400 bp and 900 bp were found in BglII and BstYI templates. The PCR products were purified from a low-melting agarose gel and sequenced with primers 228-130 and 228-129. The BglII PCR DNA did not yield any readable sequence and the BstYI PCR DNA yielded about 380 bp new DNA sequence. A stop codon had not been detected in the new sequence.

A fourth set of inverse PCR primers with the following sequences were made:
5' ctctatcctcaatcattccaattg 3' (229-42) (SEQ ID NO:30)
5' ttgagagctttgttagtgctacct 3' (229-43) (SEQ ID NO:31)

The genomic DNA was digested with ApoI, BsrFI, ClaI, HindIII, MfeI, NcoI, SalI and TseI, respectively. The digested DNA was purified through Qiagen spin columns. Self-ligation was set up at a low DNA concentration at 2 μg/ml overnight at 16° C. T4 DNA ligase was inactivated at 65° C. for 30 min and 10 μl of the ligated product was used as the template for inverse PCR. PCR conditions were 95° C. 30 sec, 55° C. 1 min, 72° C. 2 min for 35 cycles. PCR products of ~3000 bp and 1500 bp were found in ClaI and HindIII templates. The PCR products were purified from a low-melting agarose gel and sequenced with primers 229-42 and 43. It generated about 230 bp new DNA sequence. A stop codon had not been detected in the new sequence.

A fifth set of inverse PCR primers with the following sequences were made:
5' gaataatcccctaccaacaggt 3' (229-140) (SEQ ID NO:32)
5' tctatcttgcttagagctagc 3' (229-141) (SEQ ID NO:33)

The genomic DNA was digested with AgeI, BglII, ClaI, MfeI, NcoI, MheI, SacI, and SalI, respectively. The digested DNA was purified through Qiagen spin columns. Self-ligation was set up at a low DNA concentration at 2 μg/ml overnight at 16° C. T4 DNA ligase was inactivated at 65° C. for 30 min and 10 μl of the ligated product was used as the template for inverse PCR. PCR conditions were 95° C. 30 sec, 55° C. 1 min, 72° C. 2 min for 35 cycles. PCR products of ~2700 bp was found in BglII template. The PCR product was purified from a low-melting agarose gel and sequenced with primers 229-140 and 141. The entire 2.7 kb was sequenced by 8 more sequencing primers. A stop codon was found in the newly derived sequence. The entire bseRI endonuclease gene is 3345 bp, encoding a protein with 1114 amino acid with predicted molecular mass of 125 kDa.

7. Inverse PCR amplification of bseRIM gene

Because R-M genes in a particular R-M system are usually located in close proximity, efforts were made to identify the adjacent DNA sequences. A set of inverse PCR primers with the following sequences were made based on the sequence upstream of bseRIR gene:
5' gaccttgtgggtgaataaggaaac 3' (233-53) (SEQ ID NO:34)
5' gagaagttagcatcaataactgta 3' (233-54) (SEQ ID NO:35)

The genomic DNA was digested with AflIII, AvrII, BglII, DraI, HhaI, HindIII, KpnI, NdeI, NheI, NspI, StyI, and XbaI, respectively. The digested DNA was purified through Qiagen spin columns. Self-ligation was set up at a low DNA concentration at 2 μg/ml overnight at 16° C. T4 DNA ligase was inactivated at 65° C. for 30 min and 10 μl of the self-ligated product was used as the template for inverse PCR. PCR conditions were 95° C. 30 sec, 55° C. 30 sec, 72° C. 1 min for 35 cycles. PCR products of 1400 bp and 1600 bp were found in HindIII and NheI templates. The PCR product was purified from a low-melting agarose gel and sequenced with primers 233-53 and 54 and new primers, which generated ~1200 bp of new sequence for the bseRIM gene.

A second set of inverse PCR primers with the following sequences were made:
5' tacagcctcttctgtaattgatc 3' (233-233) (SEQ ID NO:36)
5' cttccttctgcaattgttgctagc 3' (233-234) (SEQ ID NO:37)

The genomic DNA was digested with AseI, HaeIII, MseI, MscI, Sau3AI, StyI, TaqI, and XbaI, respectively. The digested DNA was purified through Qiagen spin columns. Self-ligation was set up at a low DNA concentration at 2 μg/ml overnight at 16° C. T4 DNA ligase was inactivated at 65° C. for 30 min and 10 μl of the self-ligated product was used as the template for inverse PCR. PCR conditions were 95° C. 30 sec, 55° C. 30 sec, 72° C. 1 min for 35 cycles. PCR products of 500 bp, 1.2 kb, and 400 bp were found in Sau3AI, StyI, and TaqI templates. The StyI PCR product was purified from a low-melting agarose gel and sequenced with primers 233-233 and 234 and new primers, which generated ~1100 bp of new sequence for the bseRIM gene.

A third set of inverse PCR primers with the following sequences were made:

5' aagggaataactcatgcccat 3' (234-239) (SEQ ID NO:38)
5' gtgatatcctgctctatataaatc 3' (234-240) (SEQ ID NO:39)

The genomic DNA was digested with ApoI, BamHI, BglII, BstYI, BsrGI, HincII, MfeI, NspI, SpeI, TaqI, and XbaI, respectively. The digested DNA was purified through a Qiagen spin column. Self-ligation was set up at a low DNA concentration at 2 μg/ml overnight at 16° C. T4 DNA ligase was inactivated at 65° C. for 30 min and 10 μl of the self-ligated product was used as the template for inverse PCR. PCR conditions were 95° C. 30 sec, 55° C. 30 sec, 72° C. 1 min for 35 cycles. PCR products of 700 bp and 300 bp were found in TaqI and ApoI templates. Both PCR product were purified from a low-melting agarose gel and sequenced with primers 234-239 and 240, which generated ~450 bp of new sequence for the bseRIM gene.

A fourth set of inverse PCR primers with the following sequences were made:

5' gtgttcagattgtaacaaagaagtagc 3' (235-83) (SEQ ID NO:40)
5' acgtcactccaaatactgtgtcga 3' (235-84) (SEQ ID NO:41)

The genomic DNA was digested with AluI, ApoI, BamHI, BglII, BstYI, ClaI, DdeI, DraI, EcoRV, HinfI, HincII, MfeI, NcoI, NlaIII, NspI, Sau3AI, SpeI, SspI, StyI, and TfiI, respectively. The digested DNA was purified through a Qiagen spin column. Self-ligation was set up at a low DNA concentration at 2 μg/ml overnight at 16° C. T4 DNA ligase was inactivated at 65° C. for 30 min and 10 μl of the self-ligated product was used as the template for inverse PCR. PCR conditions were 95° C. 30 sec, 55° C. 30 sec, 72° C. 1 min for 35 cycles. A 2500 bp PCR product was found in the NspI template. The PCR product was purified from a low-melting agarose gel and sequenced with primers 235-83 and 84, which generated ~500 bp of new sequence for the bseRIM gene. A start codon was found for the large open reading frame of 3930 bp. This large ORF encodes two amino-methylases (a N4 cytosine methylase and a N6 adenine methylasse) that fused together to form BseRI methylase. It is one of the largest type II methylases.

8. Expression of BseRIM gene in *E. coli*

Two primers with the following sequences were synthesized:

5' tatatcgcatgcggaggtaaaaaaatgaagggaaatcagataatagacaac 3' (235-253) (SEQ ID NO:42)
5'gtcgacgcatgcttatttatttctaaaagaaagcttttc 3' (247-347) (underlined bp, SphI site) (SEQ ID NO:43)

The BseRIM gene was amplified by PCR from genomic DNA using Vent DNA polymerase. PCR conditions were 94° C. 2 min for 1 cycle, 94° C. 1 min, 55° C. 1 min, 72° C. 4 min for 30 cycles. The PCR DNA was purified by phenol-$CH_3Cl$ extraction and ethanol precipitation and then digested with SphI. The resulting DNA was ligated to CIP-treated pACYC184 with compatible ends. The ligated DNA was transferred into *E. coli* ER2683 by transformation and selected for $Cm^R$ transformants. After screening 36 plasmids, 10 plasmids demonstrated resistance to BseRI digestion, indicating the 2 BseRI sites in the vector has been fully modified by BseRI methylase. The resistant plasmid was used to transform ER2566 to generate the premodified expression host ER2566 [pACYC-BseRIM].

9. Expression of BseRI Endonuclease in E. coli.

BseRI endonuclease is a fusion of three domains, a restriction domain fused with a conserved amino-methylase domain plus specificity domain. This type enzyme has been termed type F (or type IV), with F standing for fusion of restriction and methylase/specificity domains. The type F enzymes are a subset of type IIs restriction enzymes that usually cut further downstream of their recognition sequences. For example, the prototype Eco57I (5' CTGAAG 3' N16/N14), BpmI and GsuI cut 16 and 14 bp downstream of their recognition sequences (5' CTGGAG 3' $N_{16}/N_{14}$ (SEQ ID NO:44)). Because the recognition sequence and cleavage sequence are far apart, it may require a large protein to perform such function.

Two PCR primers were synthesized with the following sequence:

5' ggagagaatcatatgaacaatagtgaaaagcaagttgag 3' (247-348) (SEQ ID NO:45)
5' ctaggatccttaaactccataaagattacggcacgc 3' (247-349) (SEQ ID NO:46)

The bseRIR gene was amplified by PCR from genomic DNA using Vent DNA polymerase. PCR conditions were 94° C. 2 min for 1 cycle, 95° C. 1 min, 55° C. 1 min, 72° C. 4 min for 25 cycles. The PCR DNA was purified by phenol-$CH_3Cl$ extraction and ethanol precipitation and then digested with NdeI and BamHI. Following purification through Qiagen spin column, the PCR DNA was ligated to a T7 expression vector pAII17 and the ligated DNA was used to transform pre-modified host ER2566 [pACYC-BseRIM]. $AP^R$ and $Cm^R$ transformants were selected and plasmids were screened for bserRIR gene insert. After screening four batches of plasmids for PCR insert, the clones with inserts were induced with IPTG and cell extracts were prepared and assayed for BseRI endonuclease activity on lambda DNA. The results were shown below:

| Experiment | Plamids | clones with insert | BseRI activity |
| --- | --- | --- | --- |
| Experiment 1 | 36 | 7 | 2 active |
| Experiment 2 | 18 | 4 | 1 active |
| Experiment 3 | 36 | 2 | 1 active |
| Experiment 4 | 36 | 2 | 1 active |

Cell extracts from 10 ml and 500 ml of IPTG-induced cell cultures were prepared and assayed for BseRI endonuclease activity. IPTG was added at 0.5 mM final concentration to late log phase cell cultures and the induced cells were cultured for 3 h at 37° C. The protein expression profiles of the induced and non-induced cell extracts were shown in FIG. 4. An induced protein band of approximately 125 kDa was detected in the IPTG-induced cell extract, but absent in the non-induced. One of the clones that displayed high BseRI activity in cell extract was shown in FIG. 5.

The strain NEB#1341, ER2566 [pACYC-BseRIM, pAII17-BseRI] has been deposited under the terms and conditions of the Budapest Treaty with the American Type Culture Collection on Sep. 28, 2001 and received ATCC Accession No. PTA-3738.

What is claimed is:

1. Isolated DNA coding for the BseRI restriction endonuclease, wherein the isolated DNA is obtainable from Bacillus species R.

2. A recombinant DNA vector comprising a vector into which a DNA segment encoding the BseRI restriction endonuclease has been inserted.

3. Isolated DNA encoding the BseRI restriction endonuclease and BseRI methylase, wherein the isolated DNA is obtainable from ATCC No. PTA-3738.

4. A vector which comprises the isolated DNA of claim 3.

5. A host cell transformed by the vector of claims 2 or 4.

6. A method of producing recombinant BseRI restriction endonuclease comprising culturing a host cell transformed with the vector of claims 2 or 4 under conditions suitable for expression of said endonuclease.

* * * * *

SEQUENCE LISTING

```
<160> NUMBER OF SEQ ID NOS: 45

<210> SEQ ID NO 1
<211> LENGTH: 6
<212> TYPE: DNA
<213> ORGANISM: Bacillus species R (CAMB2669)

<400> SEQUENCE: 1 gaggag                                                                  6

<210> SEQ ID NO 2
<211> LENGTH: 6
<212> TYPE: DNA
<213> ORGANISM: Bacillus species R (CAMB2669)

<400> SEQUENCE: 2 ctcctc                                                                  6

<210> SEQ ID NO 3
<211> LENGTH: 6
<212> TYPE: DNA
<213> ORGANISM: Deinococcus radiophilus

<400> SEQUENCE: 3 tttaaa                                                                  6

<210> SEQ ID NO 4
<211> LENGTH: 5
<212> TYPE: DNA
<213> ORGANISM: Deinococcus radiophilus
<220> FEATURE:
<221> NAME/KEY: misc_feature
<222> LOCATION: (3)..(3)
<223> OTHER INFORMATION: N=G, A, C or T

<400> SEQUENCE: 4 ggncc                                                                   5

<210> SEQ ID NO 5
<211> LENGTH: 9
<212> TYPE: DNA
<213> ORGANISM: Deinoccocus radiophilus
<220> FEATURE:
<221> NAME/KEY: misc_feature
<222> LOCATION: (4)..(6)
<223> OTHER INFORMATION: N=G, A, C, or T

<400> SEQUENCE: 5 cacnnngtg                                                               9

<210> SEQ ID NO 6
<211> LENGTH: 6
<212> TYPE: DNA
<213> ORGANISM: Escherichia coli

<400> SEQUENCE: 6 gaattc                                                                  6

<210> SEQ ID NO 7
<211> LENGTH: 5
<212> TYPE: DNA
<213> ORGANISM: Escherichia coli
<220> FEATURE:
<221> NAME/KEY: misc_feature
```

```
<222> LOCATION: (3)..(3)
<223> OTHER INFORMATION: W=A or T

<400> SEQUENCE: 7 ccwgg                                                                       5

<210> SEQ ID NO 8
<211> LENGTH: 8
<212> TYPE: DNA
<213> ORGANISM: Nocardia otitidis-caviarum

<400> SEQUENCE: 8 gcggccgc                                                                    8

<210> SEQ ID NO 9
<211> LENGTH: 3930
<212> TYPE: DNA
<213> ORGANISM: Bacillus species R (CAMB2669)
<220> FEATURE:
<221> NAME/KEY: CDS
<222> LOCATION: (1)..(3927)
<223> OTHER INFORMATION:

<400> SEQUENCE: 9 atg aag gga aat cag ata ata gac aac tca aat aac ctc tca tta aat          48
Met Lys Gly Asn Gln Ile Ile Asp Asn Ser Asn Asn Leu Ser Leu Asn
1               5                   10                  15 tct aat gaa tcg ttg ttt aat tta tat tct caa ccg cta cca gct tca          96
Ser Asn Glu Ser Leu Phe Asn Leu Tyr Ser Gln Pro Leu Pro Ala Ser
                20                  25                  30 agg agc ggt gct tta tac aat gca ttt tct tat cct aca aag ata tct         144
Arg Ser Gly Ala Leu Tyr Asn Ala Phe Ser Tyr Pro Thr Lys Ile Ser
            35                  40                  45 cca gaa tct att gca gtt ttt att gct tct cat act aaa cca gga gat         192
Pro Glu Ser Ile Ala Val Phe Ile Ala Ser His Thr Lys Pro Gly Asp
        50                  55                  60 gtt gta cta gat acc ttt ggt gga agt ggt aca act gga att gca gcg         240
Val Val Leu Asp Thr Phe Gly Gly Ser Gly Thr Thr Gly Ile Ala Ala
65                  70                  75                  80 cat tta tgt gct aac cca aca aaa gaa gtt att gat tta gct gag caa         288
His Leu Cys Ala Asn Pro Thr Lys Glu Val Ile Asp Leu Ala Glu Gln
                85                  90                  95 ctt aag gca cca gtg gaa tgg gga cct aga act gca ata att tat gag         336
Leu Lys Ala Pro Val Glu Trp Gly Pro Arg Thr Ala Ile Ile Tyr Glu
                100                 105                 110 ctt agt acg ctg gga tct ttc gtt ggg cgt aca ata aca act caa aca         384
Leu Ser Thr Leu Gly Ser Phe Val Gly Arg Thr Ile Thr Thr Gln Thr
            115                 120                 125 gat tct aag gaa ttt tta aaa agt gca gaa gaa ctt ata aag aaa tgt         432
Asp Ser Lys Glu Phe Leu Lys Ser Ala Glu Glu Leu Ile Lys Lys Cys
        130                 135                 140 gaa cag gaa gtt gga aac att tat aaa gca aga gat gat aaa ggg gat         480
Glu Gln Glu Val Gly Asn Ile Tyr Lys Ala Arg Asp Asp Lys Gly Asp
145                 150                 155                 160 tta gga aca att cga cac agt att tgg agt gac gtt tta aag tgt tca         528
Leu Gly Thr Ile Arg His Ser Ile Trp Ser Asp Val Leu Lys Cys Ser
                165                 170                 175 gat tgt aac aaa gaa gta gca ttt tgg gat gtg gct gtt caa caa tct         576
Asp Cys Asn Lys Glu Val Ala Phe Trp Asp Val Ala Val Gln Gln Ser
                180                 185                 190 cct ttg aaa ata ttg gat aaa ttt aaa tgt cct tcg tgt ggc ttt gaa         624
Pro Leu Lys Ile Leu Asp Lys Phe Lys Cys Pro Ser Cys Gly Phe Glu
```

-continued

|  |  |  |  |  |  |  |  |  |  |  |  |  |  |  |  |  |
|---|---|---|---|---|---|---|---|---|---|---|---|---|---|---|---|---|
|  |  | 195 |  |  |  | 200 |  |  |  |  | 205 |  |  |  |  |  |
| gct | gga | ata | aat | caa | gtt | gag | cgt | gtt | ttt | gaa | cct | tat | ttt | gat | gaa | 672 |
| Ala | Gly | Ile | Asn | Gln | Val | Glu | Arg | Val | Phe | Glu | Pro | Tyr | Phe | Asp | Glu |  |
|  | 210 |  |  |  | 215 |  |  |  |  | 220 |  |  |  |  |  |  |
| ttg | cta | gga | aaa | gaa | caa | ata | aga | aaa | aaa | aga | gtt | ctt | aaa | aga | ata | 720 |
| Leu | Leu | Gly | Lys | Glu | Gln | Ile | Arg | Lys | Lys | Arg | Val | Leu | Lys | Arg | Ile |  |
| 225 |  |  |  |  | 230 |  |  |  |  | 235 |  |  |  |  | 240 |  |
| tac | gga | cag | act | ggt | aag | cgg | aat | tgg | caa | cgc | cct | gct | aat | gca | gag | 768 |
| Tyr | Gly | Gln | Thr | Gly | Lys | Arg | Asn | Trp | Gln | Arg | Pro | Ala | Asn | Ala | Glu |  |
|  |  |  | 245 |  |  |  |  | 250 |  |  |  |  | 255 |  |  |  |
| gat | gaa | gat | tta | att | aag | aat | att | gaa | agt | atg | cct | ctt | ccg | aaa | gat | 816 |
| Asp | Glu | Asp | Leu | Ile | Lys | Asn | Ile | Glu | Ser | Met | Pro | Leu | Pro | Lys | Asp |  |
|  |  | 260 |  |  |  |  | 265 |  |  |  |  | 270 |  |  |  |  |
| att | cca | ctt | caa | cag | att | cca | tgg | gga | gat | tta | tat | aga | gca | gga | tat | 864 |
| Ile | Pro | Leu | Gln | Gln | Ile | Pro | Trp | Gly | Asp | Leu | Tyr | Arg | Ala | Gly | Tyr |  |
|  | 275 |  |  |  |  | 280 |  |  |  |  | 285 |  |  |  |  |  |
| cac | aag | gga | ata | act | cat | gcc | cat | cat | ttt | tat | aca | aca | aga | aat | tta | 912 |
| His | Lys | Gly | Ile | Thr | His | Ala | His | His | Phe | Tyr | Thr | Thr | Arg | Asn | Leu |  |
| 290 |  |  |  |  | 295 |  |  |  |  | 300 |  |  |  |  |  |  |
| ata | gtg | atg | gca | aca | ctg | tgg | gaa | ggc | att | aaa | tcg | gca | cct | gcg | gaa | 960 |
| Ile | Val | Met | Ala | Thr | Leu | Trp | Glu | Gly | Ile | Lys | Ser | Ala | Pro | Ala | Glu |  |
| 305 |  |  |  | 310 |  |  |  |  | 315 |  |  |  |  | 320 |  |  |
| tta | caa | gat | gcc | cta | aaa | tta | tta | gtt | cta | agt | tac | aat | tct | aca | cat | 1008 |
| Leu | Gln | Asp | Ala | Leu | Lys | Leu | Leu | Val | Leu | Ser | Tyr | Asn | Ser | Thr | His |  |
|  |  |  | 325 |  |  |  |  | 330 |  |  |  |  | 335 |  |  |  |
| tct | aca | ttg | atg | acc | aga | gta | gta | gtg | aag | tcg | aac | caa | cca | gat | ttt | 1056 |
| Ser | Thr | Leu | Met | Thr | Arg | Val | Val | Val | Lys | Ser | Asn | Gln | Pro | Asp | Phe |  |
|  |  | 340 |  |  |  |  | 345 |  |  |  |  | 350 |  |  |  |  |
| gtt | tta | act | agt | gct | caa | tct | ggg | gtt | ctg | tac | att | agt | agt | tta | cct | 1104 |
| Val | Leu | Thr | Ser | Ala | Gln | Ser | Gly | Val | Leu | Tyr | Ile | Ser | Ser | Leu | Pro |  |
|  | 355 |  |  |  |  | 360 |  |  |  |  | 365 |  |  |  |  |  |
| gta | gaa | aaa | aat | tta | ttt | gaa | ggc | tta | aag | cgg | aaa | gct | aaa | aca | att | 1152 |
| Val | Glu | Lys | Asn | Leu | Phe | Glu | Gly | Leu | Lys | Arg | Lys | Ala | Lys | Thr | Ile |  |
|  | 370 |  |  |  |  | 375 |  |  |  |  | 380 |  |  |  |  |  |
| gga | aaa | gca | ttt | gct | att | tta | gaa | aat | agc | gac | agt | aat | gta | acc | gta | 1200 |
| Gly | Lys | Ala | Phe | Ala | Ile | Leu | Glu | Asn | Ser | Asp | Ser | Asn | Val | Thr | Val |  |
| 385 |  |  |  | 390 |  |  |  |  | 395 |  |  |  |  | 400 |  |  |
| gtt | aac | gga | act | agt | aca | gat | ctt | gat | ata | cca | gat | aaa | tct | gta | gac | 1248 |
| Val | Asn | Gly | Thr | Ser | Thr | Asp | Leu | Asp | Ile | Pro | Asp | Lys | Ser | Val | Asp |  |
|  |  |  | 405 |  |  |  |  | 410 |  |  |  |  | 415 |  |  |  |
| tat | gtt | ttt | acg | gat | cct | ccg | ttt | gga | gat | tat | att | cct | tat | gcg | gaa | 1296 |
| Tyr | Val | Phe | Thr | Asp | Pro | Pro | Phe | Gly | Asp | Tyr | Ile | Pro | Tyr | Ala | Glu |  |
|  |  | 420 |  |  |  |  | 425 |  |  |  |  | 430 |  |  |  |  |
| cta | aat | ttt | ctt | aac | gag | gta | tgg | cta | ggt | aaa | aca | act | aat | cgt | act | 1344 |
| Leu | Asn | Phe | Leu | Asn | Glu | Val | Trp | Leu | Gly | Lys | Thr | Thr | Asn | Arg | Thr |  |
|  | 435 |  |  |  |  | 440 |  |  |  |  | 445 |  |  |  |  |  |
| aat | gaa | att | att | att | agt | cca | aag | cag | gaa | aaa | tcg | gtt | act | acc | tat | 1392 |
| Asn | Glu | Ile | Ile | Ile | Ser | Pro | Lys | Gln | Glu | Lys | Ser | Val | Thr | Thr | Tyr |  |
| 450 |  |  |  |  | 455 |  |  |  |  | 460 |  |  |  |  |  |  |
| gcg | gag | ttg | atg | gct | ggt | gtt | ttt | aaa | gag | att | tct | cga | aca | tta | aaa | 1440 |
| Ala | Glu | Leu | Met | Ala | Gly | Val | Phe | Lys | Glu | Ile | Ser | Arg | Thr | Leu | Lys |  |
| 465 |  |  |  | 470 |  |  |  |  | 475 |  |  |  |  | 480 |  |  |
| aat | gat | ggt | gca | gct | acg | gta | gtg | ttt | cat | tct | gca | aaa | gca | gaa | gta | 1488 |
| Asn | Asp | Gly | Ala | Ala | Thr | Val | Val | Phe | His | Ser | Ala | Lys | Ala | Glu | Val |  |
|  |  |  | 485 |  |  |  |  | 490 |  |  |  |  | 495 |  |  |  |
| tgg | aaa | tca | tta | caa | gac | tct | tat | aaa | cat | gca | ggt | tta | aag | gta | aag | 1536 |
| Trp | Lys | Ser | Leu | Gln | Asp | Ser | Tyr | Lys | His | Ala | Gly | Leu | Lys | Val | Lys |  |
|  |  |  | 500 |  |  |  |  | 505 |  |  |  |  | 510 |  |  |  |
| tat | tca | agt | gtg | ctt | gat | aag | tta | cag | gga | agt | ttt | aaa | caa | gta | tct | 1584 |

| | | | | | | | | | | | | | |
|---|---|---|---|---|---|---|---|---|---|---|---|---|---|
| Tyr | Ser | Ser | Val | Leu | Asp | Lys | Leu | Gln | Gly | Ser | Phe | Lys | Gln | Val | Ser |
| | 515 | | | | 520 | | | | | 525 | | | |

```
aaa agt gtt tct gtt aaa gga gat cct ctc ttg tat ctt aca aaa gag    1632
Lys Ser Val Ser Val Lys Gly Asp Pro Leu Leu Tyr Leu Thr Lys Glu
    530             535             540 gaa cgt aat tct gtc ctt gaa cct tcc cat att gat att gaa gct act    1680
Glu Arg Asn Ser Val Leu Glu Pro Ser His Ile Asp Ile Glu Ala Thr
545             550             555             560 ata tca cag cta ctt caa gaa gca att gct tct aaa gat gat aaa gaa    1728
Ile Ser Gln Leu Leu Gln Glu Ala Ile Ala Ser Lys Asp Asp Lys Glu
                565             570             575 cgt aca gtg gaa aga att tat act cgt ttt ata tcg aaa ttt tta gaa    1776
Arg Thr Val Glu Arg Ile Tyr Thr Arg Phe Ile Ser Lys Phe Leu Glu
            580             585             590 agt gga caa gag gtt cct ctt gat gca gct gat ttt tat cgt aaa gtg    1824
Ser Gly Gln Glu Val Pro Leu Asp Ala Ala Asp Phe Tyr Arg Lys Val
        595             600             605 aaa cca ttg ctt aaa ata agt gat ttt aga aac gaa gtc cca att cca    1872
Lys Pro Leu Leu Lys Ile Ser Asp Phe Arg Asn Glu Val Pro Ile Pro
    610             615             620 aaa gat ata aag ata caa att aat cca gaa cga caa aaa agg ttg gga    1920
Lys Asp Ile Lys Ile Gln Ile Asn Pro Glu Arg Gln Lys Arg Leu Gly
625             630             635             640 caa tat ttt act agt gga ccg tta gct gag ctg cta gca aca ttt gca    1968
Gln Tyr Phe Thr Ser Gly Pro Leu Ala Glu Leu Leu Ala Thr Phe Ala
                645             650             655 gaa gga agt aca gcc tct tct gta att gat ccg atg tgt ggc caa gga    2016
Glu Gly Ser Thr Ala Ser Ser Val Ile Asp Pro Met Cys Gly Gln Gly
            660             665             670 gat atg ctt aca gcg gtt aat tcg att aat tca aaa gca aac ctt tct    2064
Asp Met Leu Thr Ala Val Asn Ser Ile Asn Ser Lys Ala Asn Leu Ser
        675             680             685 ggc ata gac att gat cca att gct atg aat aaa tgt att gat cgt tta    2112
Gly Ile Asp Ile Asp Pro Ile Ala Met Asn Lys Cys Ile Asp Arg Leu
    690             695             700 ggt aat caa aaa aaa tct cta gac tta ata att ggg agt gcc ttc agt    2160
Gly Asn Gln Lys Lys Ser Leu Asp Leu Ile Ile Gly Ser Ala Phe Ser
705             710             715             720 tgg aat acg att aag caa tta aaa ttg aaa agt ttt gac ctt gta att    2208
Trp Asn Thr Ile Lys Gln Leu Lys Leu Lys Ser Phe Asp Leu Val Ile
                725             730             735 acg aat cct ccg tat gtt agg tat caa tca ctt tct tcg aag ttg gaa    2256
Thr Asn Pro Pro Tyr Val Arg Tyr Gln Ser Leu Ser Ser Lys Leu Glu
            740             745             750 gga gac gtg tta tta cct gat tca gaa aca gtg aga aat gat tta ctt    2304
Gly Asp Val Leu Leu Pro Asp Ser Glu Thr Val Arg Asn Asp Leu Leu
        755             760             765 gag gtt gta tct caa ctt gat cac tta gag cat aga gat aaa gaa gtg    2352
Glu Val Val Ser Gln Leu Asp His Leu Glu His Arg Asp Lys Glu Val
    770             775             780 ttt aga aca gta att aag tct tat tct ggc tta tct gat tta gcg gta    2400
Phe Arg Thr Val Ile Lys Ser Tyr Ser Gly Leu Ser Asp Leu Ala Val
785             790             795             800 cct tcg tgg ata tta tgt gca atg ctt aca tca gtt gga gga cat tta    2448
Pro Ser Trp Ile Leu Cys Ala Met Leu Thr Ser Val Gly Gly His Leu
                805             810             815 gct atg gtg gtg cct gaa tca tgg tta aat aga gat tat gcc cac cct    2496
Ala Met Val Val Pro Glu Ser Trp Leu Asn Arg Asp Tyr Ala His Pro
            820             825             830
```

```
att cat tac ttg tta ctc aag ctt ttc aag att aaa tgg gtt gtt gaa          2544
Ile His Tyr Leu Leu Leu Lys Leu Phe Lys Ile Lys Trp Val Val Glu
        835                 840                 845 gat gtc aat cgt aca tgg ttt aaa gat gcg caa gta aag aca aat tta          2592
Asp Val Asn Arg Thr Trp Phe Lys Asp Ala Gln Val Lys Thr Asn Leu
850                 855                 860 gtt gta gct gag aga att tca tat gta gaa gat att ata gaa aaa tgt          2640
Val Val Ala Glu Arg Ile Ser Tyr Val Glu Asp Ile Ile Glu Lys Cys
865                 870                 875                 880 caa ata gaa aag tat cta cat gtg gct ctt cca gaa att tta gct gac          2688
Gln Ile Glu Lys Tyr Leu His Val Ala Leu Pro Glu Ile Leu Ala Asp
                885                 890                 895 tca tct agt ata gtt ggc ggt tta ttt ccg ggc tca gta acc cca aac          2736
Ser Ser Ser Ile Val Gly Gly Leu Phe Pro Gly Ser Val Thr Pro Asn
            900                 905                 910 gaa gat ttt tat aat ttg tta aag agg gta aaa ggt aac tct gat tta          2784
Glu Asp Phe Tyr Asn Leu Leu Lys Arg Val Lys Gly Asn Ser Asp Leu
        915                 920                 925 gaa att atg aag ttc cca ata atg tat cga aat att aaa act aaa tta          2832
Glu Ile Met Lys Phe Pro Ile Met Tyr Arg Asn Ile Lys Thr Lys Leu
930                 935                 940 gat gat ttc att gct act tca ttt aat tca gag tgg ttt aga agc tgt          2880
Asp Asp Phe Ile Ala Thr Ser Phe Asn Ser Glu Trp Phe Arg Ser Cys
945                 950                 955                 960 gaa ccg aat ctt gtg aaa caa att aag aat caa agg cta aaa ggc aag          2928
Glu Pro Asn Leu Val Lys Gln Ile Lys Asn Gln Arg Leu Lys Gly Lys
                965                 970                 975 agc agt aca gtt aaa atg cca caa cag tta cta gat gtt gtt cag att          2976
Ser Ser Thr Val Lys Met Pro Gln Gln Leu Leu Asp Val Val Gln Ile
            980                 985                 990 agt aat att gat ttt tgc tca att  gaa gac cta gga tgg  aag gtt gga        3024
Ser Asn Ile Asp Phe Cys Ser Ile  Glu Asp Leu Gly Trp  Lys Val Gly
        995                 1000                1005 caa ggc  tta aga aca ggt gct  aat tct ttc ttt tac  tgt gat gtt           3069
Gln Gly  Leu Arg Thr Gly Ala  Asn Ser Phe Phe Tyr  Cys Asp Val
    1010                1015                1020 ata aat  gaa aca gaa gaa tac  agt acg gtg gtt aca  agc aaa aag           3114
Ile Asn  Glu Thr Glu Glu Tyr  Ser Thr Val Val Thr  Ser Lys Lys
    1025                1030                1035 ttg ggg  tca agg acc ttt aat  ttg cct aag gat gca  tta ttg cct           3159
Leu Gly  Ser Arg Thr Phe Asn  Leu Pro Lys Asp Ala  Leu Leu Pro
    1040                1045                1050 gtt tta  aga aaa caa aat gaa  att aaa gat aat ttt  tta ttg ctt           3204
Val Leu  Arg Lys Gln Asn Glu  Ile Lys Asp Asn Phe  Leu Leu Leu
    1055                1060                1065 caa aac  cag tta tat gga aga  gtt ctt ttt tta gaa  aat tat att           3249
Gln Asn  Gln Leu Tyr Gly Arg  Val Leu Phe Leu Glu  Asn Tyr Ile
    1070                1075                1080 cat cca  caa gac ttg tca aaa  att agt gag agt tta  ata tta cct           3294
His Pro  Gln Asp Leu Ser Lys  Ile Ser Glu Ser Leu  Ile Leu Pro
    1085                1090                1095 ata gat  att ggt cga aaa gtc  atg cct tta gaa atg  cag aat cta           3339
Ile Asp  Ile Gly Arg Lys Val  Met Pro Leu Glu Met  Gln Asn Leu
    1100                1105                1110 atc gat  ttg gct act gat ata  aat gta ggg aca atg  gaa aag cca           3384
Ile Asp  Leu Ala Thr Asp Ile  Asn Val Gly Thr Met  Glu Lys Pro
    1115                1120                1125 aaa ttt  ata cct agt tta tct  gca gtt cgg act aat  gta act aag           3429
Lys Phe  Ile Pro Ser Leu Ser  Ala Val Arg Thr Asn  Val Thr Lys
    1130                1135                1140
```

-continued

```
caa caa gac gtc aat gcg aga ttt tgg tat atg ctt cca cga ttg      3474
Gln Gln Asp Val Asn Ala Arg Phe Trp Tyr Met Leu Pro Arg Leu
    1145                1150                1155 act ggt aga cat aaa tca gaa tta ttt att cct cgt att aat aac      3519
Thr Gly Arg His Lys Ser Glu Leu Phe Ile Pro Arg Ile Asn Asn
1160                1165                1170 ttg cac cca aaa act ttg ttg aat tct aac aat aca gtt att gat      3564
Leu His Pro Lys Thr Leu Leu Asn Ser Asn Asn Thr Val Ile Asp
    1175                1180                1185 gct aac ttc tcg acc ttg tgg gtg aat aag gaa aca ata gta gat      3609
Ala Asn Phe Ser Thr Leu Trp Val Asn Lys Glu Thr Ile Val Asp
1190                1195                1200 aaa tat gct att tta gcc tta ttc aac agc aca tgg gct ata gca      3654
Lys Tyr Ala Ile Leu Ala Leu Phe Asn Ser Thr Trp Ala Ile Ala
    1205                1210                1215 ttt atg gaa tta aca gga agt gtt atg gga ggc ggt gca tta aaa      3699
Phe Met Glu Leu Thr Gly Ser Val Met Gly Gly Gly Ala Leu Lys
1220                1225                1230 tta gaa gca aca cat ctt aag cgc ctg cca att ccc gct ctt tta      3744
Leu Glu Ala Thr His Leu Lys Arg Leu Pro Ile Pro Ala Leu Leu
    1235                1240                1245 gat gag ggt tgg caa agg cta tct cac cta ggt aaa gct cta ata      3789
Asp Glu Gly Trp Gln Arg Leu Ser His Leu Gly Lys Ala Leu Ile
1250                1255                1260 tat atg gaa gat gaa ctc gaa aca ttg aaa caa ata gac gat ata      3834
Tyr Met Glu Asp Glu Leu Glu Thr Leu Lys Gln Ile Asp Asp Ile
    1265                1270                1275 att ctt aaa gct ata aca ggg aag agc aac gta ctt cct acc tta      3879
Ile Leu Lys Ala Ile Thr Gly Lys Ser Asn Val Leu Pro Thr Leu
1280                1285                1290 gag ctc tta gaa aaa att aaa atc gaa aag ctt tct ttt aga aat      3924
Glu Leu Leu Glu Lys Ile Lys Ile Glu Lys Leu Ser Phe Arg Asn
    1295                1300                1305 aaa taa                                                           3930
Lys
```

<210> SEQ ID NO 10
<211> LENGTH: 1309
<212> TYPE: PRT
<213> ORGANISM: Bacillus species R (CAMB2669)

<400> SEQUENCE: 10

```
Met Lys Gly Asn Gln Ile Ile Asp Asn Ser Asn Asn Leu Ser Leu Asn
1               5                   10                  15

Ser Asn Glu Ser Leu Phe Asn Leu Tyr Ser Gln Pro Leu Pro Ala Ser
            20                  25                  30

Arg Ser Gly Ala Leu Tyr Asn Ala Phe Ser Tyr Pro Thr Lys Ile Ser
        35                  40                  45

Pro Glu Ser Ile Ala Val Phe Ile Ala Ser His Thr Lys Pro Gly Asp
    50                  55                  60

Val Val Leu Asp Thr Phe Gly Gly Ser Gly Thr Gly Ile Ala Ala
65                  70                  75                  80

His Leu Cys Ala Asn Pro Thr Lys Glu Val Ile Asp Leu Ala Glu Gln
                85                  90                  95

Leu Lys Ala Pro Val Glu Trp Gly Pro Arg Thr Ala Ile Ile Tyr Glu
            100                 105                 110

Leu Ser Thr Leu Gly Ser Phe Val Gly Arg Thr Ile Thr Thr Gln Thr
        115                 120                 125
```

-continued

```
Asp Ser Lys Glu Phe Leu Lys Ser Ala Glu Glu Leu Ile Lys Lys Cys
    130                 135                 140
Glu Gln Glu Val Gly Asn Ile Tyr Lys Ala Arg Asp Lys Gly Asp
145                 150                 155                 160
Leu Gly Thr Ile Arg His Ser Ile Trp Ser Asp Val Leu Lys Cys Ser
                165                 170                 175
Asp Cys Asn Lys Glu Val Ala Phe Trp Asp Val Ala Val Gln Gln Ser
                180                 185                 190
Pro Leu Lys Ile Leu Asp Lys Phe Lys Cys Pro Ser Cys Gly Phe Glu
                195                 200                 205
Ala Gly Ile Asn Gln Val Glu Arg Val Phe Glu Pro Tyr Phe Asp Glu
        210                 215                 220
Leu Leu Gly Lys Glu Gln Ile Arg Lys Arg Val Leu Lys Arg Ile
225                 230                 235                 240
Tyr Gly Gln Thr Gly Lys Arg Asn Trp Gln Arg Pro Ala Asn Ala Glu
                245                 250                 255
Asp Glu Asp Leu Ile Lys Asn Ile Glu Ser Met Pro Leu Pro Lys Asp
                260                 265                 270
Ile Pro Leu Gln Gln Ile Pro Trp Gly Asp Leu Tyr Arg Ala Gly Tyr
        275                 280                 285
His Lys Gly Ile Thr His Ala His His Phe Tyr Thr Thr Arg Asn Leu
        290                 295                 300
Ile Val Met Ala Thr Leu Trp Glu Gly Ile Lys Ser Ala Pro Ala Glu
305                 310                 315                 320
Leu Gln Asp Ala Leu Lys Leu Leu Val Leu Ser Tyr Asn Ser Thr His
                325                 330                 335
Ser Thr Leu Met Thr Arg Val Val Lys Ser Asn Gln Pro Asp Phe
                340                 345                 350
Val Leu Thr Ser Ala Gln Ser Gly Val Leu Tyr Ile Ser Ser Leu Pro
        355                 360                 365
Val Glu Lys Asn Leu Phe Glu Gly Leu Lys Arg Lys Ala Lys Thr Ile
    370                 375                 380
Gly Lys Ala Phe Ala Ile Leu Glu Asn Ser Asp Ser Asn Val Thr Val
385                 390                 395                 400
Val Asn Gly Thr Ser Thr Asp Leu Asp Ile Pro Asp Lys Ser Val Asp
                405                 410                 415
Tyr Val Phe Thr Asp Pro Pro Phe Gly Asp Tyr Ile Pro Tyr Ala Glu
                420                 425                 430
Leu Asn Phe Leu Asn Glu Val Trp Leu Gly Lys Thr Thr Asn Arg Thr
                435                 440                 445
Asn Glu Ile Ile Ile Ser Pro Lys Gln Glu Lys Ser Val Thr Thr Tyr
        450                 455                 460
Ala Glu Leu Met Ala Gly Val Phe Lys Glu Ile Ser Arg Thr Leu Lys
465                 470                 475                 480
Asn Asp Gly Ala Ala Thr Val Val Phe His Ser Ala Lys Ala Glu Val
                485                 490                 495
Trp Lys Ser Leu Gln Asp Ser Tyr Lys His Ala Gly Leu Lys Val Lys
                500                 505                 510
Tyr Ser Ser Val Leu Asp Lys Leu Gln Gly Ser Phe Lys Gln Val Ser
        515                 520                 525
Lys Ser Val Ser Val Lys Gly Asp Pro Leu Leu Tyr Leu Thr Lys Glu
530                 535                 540
```

```
Glu Arg Asn Ser Val Leu Glu Pro Ser His Ile Asp Ile Glu Ala Thr
545                 550                 555                 560

Ile Ser Gln Leu Leu Gln Glu Ala Ile Ala Ser Lys Asp Asp Lys Glu
                565                 570                 575

Arg Thr Val Glu Arg Ile Tyr Thr Arg Phe Ile Ser Lys Phe Leu Glu
                580                 585                 590

Ser Gly Gln Glu Val Pro Leu Asp Ala Ala Asp Phe Tyr Arg Lys Val
            595                 600                 605

Lys Pro Leu Leu Lys Ile Ser Asp Phe Arg Asn Glu Val Pro Ile Pro
610                 615                 620

Lys Asp Ile Lys Ile Gln Ile Asn Pro Glu Arg Gln Lys Arg Leu Gly
625                 630                 635                 640

Gln Tyr Phe Thr Ser Gly Pro Leu Ala Glu Leu Leu Ala Thr Phe Ala
                645                 650                 655

Glu Gly Ser Thr Ala Ser Ser Val Ile Asp Pro Met Cys Gly Gln Gly
            660                 665                 670

Asp Met Leu Thr Ala Val Asn Ser Ile Asn Ser Lys Ala Asn Leu Ser
        675                 680                 685

Gly Ile Asp Ile Asp Pro Ile Ala Met Asn Lys Cys Ile Asp Arg Leu
690                 695                 700

Gly Asn Gln Lys Lys Ser Leu Asp Leu Ile Ile Gly Ser Ala Phe Ser
705                 710                 715                 720

Trp Asn Thr Ile Lys Gln Leu Lys Leu Lys Ser Phe Asp Leu Val Ile
                725                 730                 735

Thr Asn Pro Pro Tyr Val Arg Tyr Gln Ser Leu Ser Ser Lys Leu Glu
            740                 745                 750

Gly Asp Val Leu Leu Pro Asp Ser Glu Thr Val Arg Asn Asp Leu Leu
        755                 760                 765

Glu Val Val Ser Gln Leu Asp His Leu Glu His Arg Asp Lys Glu Val
    770                 775                 780

Phe Arg Thr Val Ile Lys Ser Tyr Ser Gly Leu Ser Asp Leu Ala Val
785                 790                 795                 800

Pro Ser Trp Ile Leu Cys Ala Met Leu Thr Ser Val Gly Gly His Leu
                805                 810                 815

Ala Met Val Val Pro Glu Ser Trp Leu Asn Arg Asp Tyr Ala His Pro
            820                 825                 830

Ile His Tyr Leu Leu Leu Lys Leu Phe Lys Ile Lys Trp Val Val Glu
        835                 840                 845

Asp Val Asn Arg Thr Trp Phe Lys Asp Ala Gln Val Lys Thr Asn Leu
850                 855                 860

Val Val Ala Glu Arg Ile Ser Tyr Val Glu Asp Ile Ile Glu Lys Cys
865                 870                 875                 880

Gln Ile Glu Lys Tyr Leu His Val Ala Leu Pro Glu Ile Leu Ala Asp
                885                 890                 895

Ser Ser Ser Ile Val Gly Gly Leu Phe Pro Gly Ser Val Thr Pro Asn
            900                 905                 910

Glu Asp Phe Tyr Asn Leu Leu Lys Arg Val Lys Gly Asn Ser Asp Leu
        915                 920                 925

Glu Ile Met Lys Phe Pro Ile Met Tyr Arg Asn Ile Lys Thr Lys Leu
    930                 935                 940

Asp Asp Phe Ile Ala Thr Ser Phe Asn Ser Glu Trp Phe Arg Ser Cys
945                 950                 955                 960

Glu Pro Asn Leu Val Lys Gln Ile Lys Asn Gln Arg Leu Lys Gly Lys
```

-continued

```
                        965                 970                 975
Ser Ser Thr Val Lys Met Pro Gln Gln Leu Leu Asp Val Val Gln Ile
                    980                 985                 990

Ser Asn Ile Asp Phe Cys Ser Ile Glu Asp Leu Gly Trp Lys Val Gly
                995                 1000                1005

Gln Gly Leu Arg Thr Gly Ala Asn Ser Phe Phe Tyr Cys Asp Val
        1010                1015                1020

Ile Asn Glu Thr Glu Glu Tyr Ser Thr Val Val Thr Ser Lys Lys
        1025                1030                1035

Leu Gly Ser Arg Thr Phe Asn Leu Pro Lys Asp Ala Leu Leu Pro
        1040                1045                1050

Val Leu Arg Lys Gln Asn Glu Ile Lys Asp Asn Phe Leu Leu Leu
        1055                1060                1065

Gln Asn Gln Leu Tyr Gly Arg Val Leu Phe Leu Glu Asn Tyr Ile
        1070                1075                1080

His Pro Gln Asp Leu Ser Lys Ile Ser Glu Ser Leu Ile Leu Pro
        1085                1090                1095

Ile Asp Ile Gly Arg Lys Val Met Pro Leu Glu Met Gln Asn Leu
        1100                1105                1110

Ile Asp Leu Ala Thr Asp Ile Asn Val Gly Thr Met Glu Lys Pro
        1115                1120                1125

Lys Phe Ile Pro Ser Leu Ser Ala Val Arg Thr Asn Val Thr Lys
        1130                1135                1140

Gln Gln Asp Val Asn Ala Arg Phe Trp Tyr Met Leu Pro Arg Leu
        1145                1150                1155

Thr Gly Arg His Lys Ser Glu Leu Phe Ile Pro Arg Ile Asn Asn
        1160                1165                1170

Leu His Pro Lys Thr Leu Leu Asn Ser Asn Asn Thr Val Ile Asp
        1175                1180                1185

Ala Asn Phe Ser Thr Leu Trp Val Asn Lys Glu Thr Ile Val Asp
        1190                1195                1200

Lys Tyr Ala Ile Leu Ala Leu Phe Asn Ser Thr Trp Ala Ile Ala
        1205                1210                1215

Phe Met Glu Leu Thr Gly Ser Val Met Gly Gly Gly Ala Leu Lys
        1220                1225                1230

Leu Glu Ala Thr His Leu Lys Arg Leu Pro Ile Pro Ala Leu Leu
        1235                1240                1245

Asp Glu Gly Trp Gln Arg Leu Ser His Leu Gly Lys Ala Leu Ile
        1250                1255                1260

Tyr Met Glu Asp Glu Leu Glu Thr Leu Lys Gln Ile Asp Asp Ile
        1265                1270                1275

Ile Leu Lys Ala Ile Thr Gly Lys Ser Asn Val Leu Pro Thr Leu
        1280                1285                1290

Glu Leu Leu Glu Lys Ile Lys Ile Glu Lys Leu Ser Phe Arg Asn
        1295                1300                1305

Lys
```

<210> SEQ ID NO 11
<211> LENGTH: 3345
<212> TYPE: DNA
<213> ORGANISM: Bacillus species R (CAMB2669)
<220> FEATURE:
<221> NAME/KEY: CDS
<222> LOCATION: (1)..(3342)
<223> OTHER INFORMATION:

<400> SEQUENCE: 11

```
atg aac aat agt gaa aag caa gtt gag cta gct aga gag tgt ata atc     48
Met Asn Asn Ser Glu Lys Gln Val Glu Leu Ala Arg Glu Cys Ile Ile
1               5                  10                  15 gct agt ttg ggc tta att cga ggg gga aaa gtc gag gac gta att cgc     96
Ala Ser Leu Gly Leu Ile Arg Gly Gly Lys Val Glu Asp Val Ile Arg
            20                  25                  30 cat agt ttt act tcc tat ttg cga act atg ttt cct gat gag cca agt    144
His Ser Phe Thr Ser Tyr Leu Arg Thr Met Phe Pro Asp Glu Pro Ser
        35                  40                  45 tgg att aaa caa cat ata gaa ggt agt gag tca gca gtc aag ttt tct    192
Trp Ile Lys Gln His Ile Glu Gly Ser Glu Ser Ala Val Lys Phe Ser
    50                  55                  60 aaa gaa gga aag ctt cgg act ggc ttt gta gat aac ttg gtt gat ctt    240
Lys Glu Gly Lys Leu Arg Thr Gly Phe Val Asp Asn Leu Val Asp Leu
65                  70                  75                  80 aca gct att gaa tat gaa tca aac atc acc aat aaa aca aag ttt gag    288
Thr Ala Ile Glu Tyr Glu Ser Asn Ile Thr Asn Lys Thr Lys Phe Glu
                85                  90                  95 aat ggt tac ggt cag gtt aaa gat tat tgt gcc tca tta tta aac aaa    336
Asn Gly Tyr Gly Gln Val Lys Asp Tyr Cys Ala Ser Leu Leu Asn Lys
            100                 105                 110 ggg tac gat tct gag cta ata ttg ggt gta ttg tct gat aca gtt aga    384
Gly Tyr Asp Ser Glu Leu Ile Leu Gly Val Leu Ser Asp Thr Val Arg
        115                 120                 125 tgg aaa gct tat aag ata aaa act ata gtt act cct gcc aat aga aag    432
Trp Lys Ala Tyr Lys Ile Lys Thr Ile Val Thr Pro Ala Asn Arg Lys
    130                 135                 140 ttt ggt cgt gac gat att gag ctt gat gag att gaa tct atc gat ttg    480
Phe Gly Arg Asp Asp Ile Glu Leu Asp Glu Ile Glu Ser Ile Asp Leu
145                 150                 155                 160 tca tta gcg gat aat tta gct gga aaa agg ctt ata gat ttt tta aac    528
Ser Leu Ala Asp Asn Leu Ala Gly Lys Arg Leu Ile Asp Phe Leu Asn
                165                 170                 175 act tac ctt ggc cga tta gga tca cga ccg ttg act gct tcc tct cta    576
Thr Tyr Leu Gly Arg Leu Gly Ser Arg Pro Leu Thr Ala Ser Ser Leu
            180                 185                 190 gcc aat gat tta ggc ttt gat agt cac ttt tgt tca cgt cat att tct    624
Ala Asn Asp Leu Gly Phe Asp Ser His Phe Cys Ser Arg His Ile Ser
        195                 200                 205 agc ctt aga gag cta gta aat aat gct ttt act caa aga cca gaa tat    672
Ser Leu Arg Glu Leu Val Asn Asn Ala Phe Thr Gln Arg Pro Glu Tyr
    210                 215                 220 ggg gaa atg att act aat cta tgg tgt aga ttt gtg agt tac cta aga    720
Gly Glu Met Ile Thr Asn Leu Trp Cys Arg Phe Val Ser Tyr Leu Arg
225                 230                 235                 240 gat aaa aat tct gtt gca gaa ttt gac aga gaa atg tat tca gat gag    768
Asp Lys Asn Ser Val Ala Glu Phe Asp Arg Glu Met Tyr Ser Asp Glu
                245                 250                 255 tta tat att tta acc ctt gca aaa ttg gta tgt gcg aat atc att gaa    816
Leu Tyr Ile Leu Thr Leu Ala Lys Leu Val Cys Ala Asn Ile Ile Glu
            260                 265                 270 aat aga gca cta cgg agt gat aga gat gaa ata tca gct ata atg caa    864
Asn Arg Ala Leu Arg Ser Asp Arg Asp Glu Ile Ser Ala Ile Met Gln
        275                 280                 285 gga gat ttt ttc aag gtc aga gga att atg aat cta gtc gaa tac gat    912
Gly Asp Phe Phe Lys Val Arg Gly Ile Met Asn Leu Val Glu Tyr Asp
    290                 295                 300
```

```
tat ttt gga tgg ctt aac gaa ggt gaa ttt ctt gaa aaa ata ata cct      960
Tyr Phe Gly Trp Leu Asn Glu Gly Glu Phe Leu Glu Lys Ile Ile Pro
305                 310                 315                 320 gtg gca caa gaa atg cag gaa gat ctt atg gct tat aat ttc tca gct     1008
Val Ala Gln Glu Met Gln Glu Asp Leu Met Ala Tyr Asn Phe Ser Ala
            325                 330                 335 ccg cct gcg gac gat tta ttc ggt caa ata atg gca cag ctt gct tct     1056
Pro Pro Ala Asp Asp Leu Phe Gly Gln Ile Met Ala Gln Leu Ala Ser
340                 345                 350 cgt tct caa aga atc tta ctt ggg cag gag tgg aca ccg aaa tgg tta     1104
Arg Ser Gln Arg Ile Leu Leu Gly Gln Glu Trp Thr Pro Lys Trp Leu
        355                 360                 365 gct agt tcc att gtc aaa cag gtt tta gaa aag tta ccg gtt gag gaa     1152
Ala Ser Ser Ile Val Lys Gln Val Leu Glu Lys Leu Pro Val Glu Glu
370                 375                 380 ttt cct aaa tta gtt gat atg tgt tgt ggt tct gga gca ctt ata gta     1200
Phe Pro Lys Leu Val Asp Met Cys Cys Gly Ser Gly Ala Leu Ile Val
385                 390                 395                 400 gaa gca ata gaa cag tca aaa gca atg ata aaa aga aac aaa att aca     1248
Glu Ala Ile Glu Gln Ser Lys Ala Met Ile Lys Arg Asn Lys Ile Thr
            405                 410                 415 agt caa tca tcc ata ggt tta gat cca act aac gga agt tct gga atg     1296
Ser Gln Ser Ser Ile Gly Leu Asp Pro Thr Asn Gly Ser Ser Gly Met
            420                 425                 430 ctt att aaa tcg ata gag gca aca caa tgt cta aat gaa ata gaa att     1344
Leu Ile Lys Ser Ile Glu Ala Thr Gln Cys Leu Asn Glu Ile Glu Ile
        435                 440                 445 gat caa gct gaa att gaa ttg ctt acc caa gca atc act ggt ttt gat     1392
Asp Gln Ala Glu Ile Glu Leu Leu Thr Gln Ala Ile Thr Gly Phe Asp
450                 455                 460 ata gac cct ttg gca gtt atg tta tcc aaa att agc tgg tta ctt gct     1440
Ile Asp Pro Leu Ala Val Met Leu Ser Lys Ile Ser Trp Leu Leu Ala
465                 470                 475                 480 gca agg gat tgg tta gag ccg ttt gga agt ttt gaa gta act att cct     1488
Ala Arg Asp Trp Leu Glu Pro Phe Gly Ser Phe Glu Val Thr Ile Pro
            485                 490                 495 gtt tat cat gct gat tca ttg ttt gct att aca cca tta tca gat gtt     1536
Val Tyr His Ala Asp Ser Leu Phe Ala Ile Thr Pro Leu Ser Asp Val
            500                 505                 510 ata ggt gaa gaa gaa caa gaa gat tgt tac caa tta caa ata gca gaa     1584
Ile Gly Glu Glu Glu Gln Glu Asp Cys Tyr Gln Leu Gln Ile Ala Glu
        515                 520                 525 gac tta att aag ctc cct aaa ttt tta att tca cct caa ttt cta aat     1632
Asp Leu Ile Lys Leu Pro Lys Phe Leu Ile Ser Pro Gln Phe Leu Asn
530                 535                 540 tat ttt gat acg tta ata gat ttc ggc tat aat att gca att aca att     1680
Tyr Phe Asp Thr Leu Ile Asp Phe Gly Tyr Asn Ile Ala Ile Thr Ile
545                 550                 555                 560 gga atg att gag gat aga gaa ctt gag agc ttt gtt agt gct acc tta     1728
Gly Met Ile Glu Asp Arg Glu Leu Glu Ser Phe Val Ser Ala Thr Leu
            565                 570                 575 aat gat tcc gag ctc gaa gtc gac agc gca atg att gta agt aca aaa     1776
Asn Asp Ser Glu Leu Glu Val Asp Ser Ala Met Ile Val Ser Thr Lys
            580                 585                 590 agg ttt cta tct tcc ttt ata tca aca gtt agc cgg ctt cat agt gag     1824
Arg Phe Leu Ser Ser Phe Ile Ser Thr Val Ser Arg Leu His Ser Glu
        595                 600                 605 gga cgg aat gga ata tgg gcc ttt att ctt cgt aac agc tat cga cca     1872
Gly Arg Asn Gly Ile Trp Ala Phe Ile Leu Arg Asn Ser Tyr Arg Pro
610                 615                 620
```

```
gga ctt gtg gca gga cag ttt aat ggc tta gta tca aat cca cca tgg   1920
Gly Leu Val Ala Gly Gln Phe Asn Gly Leu Val Ser Asn Pro Pro Trp
625                 630                 635                 640 cta gct cta agc aag ata gag aat aat ccc tac caa cag gta tta aaa   1968
Leu Ala Leu Ser Lys Ile Glu Asn Asn Pro Tyr Gln Gln Val Leu Lys
                645                 650                 655 aag aaa gca gag agg ttt gga att aaa ccg cct ggt ccg gca ttt ttg   2016
Lys Lys Ala Glu Arg Phe Gly Ile Lys Pro Pro Gly Pro Ala Phe Leu
            660                 665                 670 cat att gaa atg gca aca acc ttt tta tta cat gct gtc gat cgt tat   2064
His Ile Glu Met Ala Thr Thr Phe Leu Leu His Ala Val Asp Arg Tyr
        675                 680                 685 ctt aaa tcg ggg gct gta gta ggg tgt att aca cct gaa act gtc ctt   2112
Leu Lys Ser Gly Ala Val Val Gly Cys Ile Thr Pro Glu Thr Val Leu
    690                 695                 700 aat gga tat aat cat gaa cct ttt aga caa ttg gct ttt tcg aag acc   2160
Asn Gly Tyr Asn His Glu Pro Phe Arg Gln Leu Ala Phe Ser Lys Thr
705                 710                 715                 720 gct aac cct gta aac ttt gag ctt aac gaa att tgg aag ctt gaa gag   2208
Ala Asn Pro Val Asn Phe Glu Leu Asn Glu Ile Trp Lys Leu Glu Glu
                725                 730                 735 aat aca ttt aaa aat aag gga atc gtt ctt ttt ggc act aag agt aac   2256
Asn Thr Phe Lys Asn Lys Gly Ile Val Leu Phe Gly Thr Lys Ser Asn
            740                 745                 750 agc tca cct gta ctt cct aat cca atc cca ggt gct gta gta ggt aaa   2304
Ser Ser Pro Val Leu Pro Asn Pro Ile Pro Gly Ala Val Val Gly Lys
        755                 760                 765 aat agt tta tct ata aca agt ttt ttt atg aat acc caa ggc aaa aga   2352
Asn Ser Leu Ser Ile Thr Ser Phe Phe Met Asn Thr Gln Gly Lys Arg
    770                 775                 780 tcc gct tta tcg gat aat caa act aac cgc gac aat aag gca tcc tta   2400
Ser Ala Leu Ser Asp Asn Gln Thr Asn Arg Asp Asn Lys Ala Ser Leu
785                 790                 795                 800 tcg cct ggt tct ttt aag caa ggg gca gat aat atg cct cgg aga cta   2448
Ser Pro Gly Ser Phe Lys Gln Gly Ala Asp Asn Met Pro Arg Arg Leu
                805                 810                 815 ctg ttt cat gaa ata aca cct ata aaa tct gca aag gga ata caa cag   2496
Leu Phe His Glu Ile Thr Pro Ile Lys Ser Ala Lys Gly Ile Gln Gln
            820                 825                 830 gta agt gtg aag cct att gag gtt gga gtt agt cct tta tca ttc ata   2544
Val Ser Val Lys Pro Ile Glu Val Gly Val Ser Pro Leu Ser Phe Ile
        835                 840                 845 gta aaa gat gcg aaa aag tta tct gat ttt agg ata aat cca act gtg   2592
Val Lys Asp Ala Lys Lys Leu Ser Asp Phe Arg Ile Asn Pro Thr Val
    850                 855                 860 tta cct agt gat tta ttt tac gac gtt ttg acg tct aac atg ctt acc   2640
Leu Pro Ser Asp Leu Phe Tyr Asp Val Leu Thr Ser Asn Met Leu Thr
865                 870                 875                 880 cca ttt aat atc gtt tca ccg gtt aaa gca cta tta cca ata cgt aga   2688
Pro Phe Asn Ile Val Ser Pro Val Lys Ala Leu Leu Pro Ile Arg Arg
                885                 890                 895 gga agt aac gat aaa tgg gaa cca tta aca gaa ggt tca tta ata gct   2736
Gly Ser Asn Asp Lys Trp Glu Pro Leu Thr Glu Gly Ser Leu Ile Ala
            900                 905                 910 aaa ggt cag aga gtc aat tta gct ttt aaa cag ata ttt agc gct atg   2784
Lys Gly Gln Arg Val Asn Leu Ala Phe Lys Gln Ile Phe Ser Ala Met
        915                 920                 925 gga aat aaa gcg gat ata aat aca tta tgg aac caa ata aac aca aga   2832
Gly Asn Lys Ala Asp Ile Asn Thr Leu Trp Asn Gln Ile Asn Thr Arg
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     | 930 |     |     |     | 935 |     |     |     | 940 |     |     |     |     |     |      |
| gga | aag | ctt | gct | cag | cag | gtt | att | caa | cct | ggt | gga | tat | tta | ctg | ttt | 2880 |
| Gly | Lys | Leu | Ala | Gln | Gln | Val | Ile | Gln | Pro | Gly | Gly | Tyr | Leu | Leu | Phe |      |
| 945 |     |     |     | 950 |     |     |     | 955 |     |     |     | 960 |     |     |     |      |
| act | ggt | act | agt | ggt | gaa | aaa | gta | tgc | tca | gct | ttt | tta | gat | act | caa | 2928 |
| Thr | Gly | Thr | Ser | Gly | Glu | Lys | Val | Cys | Ser | Ala | Phe | Leu | Asp | Thr | Gln |      |
|     |     |     |     | 965 |     |     |     | 970 |     |     |     | 975 |     |     |     |      |
| aag | ata | gac | att | gag | agg | ctt | ata | att | gac | cag | acc | cta | aac | tgg | gct | 2976 |
| Lys | Ile | Asp | Ile | Glu | Arg | Leu | Ile | Ile | Asp | Gln | Thr | Leu | Asn | Trp | Ala |      |
|     |     | 980 |     |     |     | 985 |     |     |     | 990 |     |     |     |     |     |      |
| aca | gtg | gag | act | tta | gat | gaa | gca | tgt | tat | att | aca | ggc | ctt | ttc | aat | 3024 |
| Thr | Val | Glu | Thr | Leu | Asp | Glu | Ala | Cys | Tyr | Ile | Thr | Gly | Leu | Phe | Asn |      |
|     |     |     |     | 995 |     |     |     |1000 |     |     |     |1005 |     |     |     |      |
| agt | gaa | gca | att | aac | ctt | atg | ata | aag | gat | ttt | caa | cca | gag | ggt |     | 3069 |
| Ser | Glu | Ala | Ile | Asn | Leu | Met | Ile | Lys | Asp | Phe | Gln | Pro | Glu | Gly |     |      |
|     |1010 |     |     |     |1015 |     |     |     |1020 |     |     |     |     |     |     |      |
| gct | ttt | ggg | gga | cgt | cat | att | cat | tct | ctt | cct | ttc | aga | gtg | aca |     | 3114 |
| Ala | Phe | Gly | Gly | Arg | His | Ile | His | Ser | Leu | Pro | Phe | Arg | Val | Thr |     |      |
|1025 |     |     |     |1030 |     |     |     |1035 |     |     |     |     |     |     |     |      |
| cca | cgg | ttt | gat | tca | acg | caa | ccc | gct | cat | caa | gaa | gta | gta | gaa |     | 3159 |
| Pro | Arg | Phe | Asp | Ser | Thr | Gln | Pro | Ala | His | Gln | Glu | Val | Val | Glu |     |      |
|1040 |     |     |     |1045 |     |     |     |1050 |     |     |     |     |     |     |     |      |
| aaa | act | aag | ttt | tta | atc | atg | gaa | ttt | caa | ggt | tta | aag | cat | tct |     | 3204 |
| Lys | Thr | Lys | Phe | Leu | Ile | Met | Glu | Phe | Gln | Gly | Leu | Lys | His | Ser |     |      |
|1055 |     |     |     |1060 |     |     |     |1065 |     |     |     |     |     |     |     |      |
| gat | cca | aca | ata | gaa | gaa | aat | tta | ctt | aat | cct | aat | ttt | agt | act |     | 3249 |
| Asp | Pro | Thr | Ile | Glu | Glu | Asn | Leu | Leu | Asn | Pro | Asn | Phe | Ser | Thr |     |      |
|1070 |     |     |     |1075 |     |     |     |1080 |     |     |     |     |     |     |     |      |
| ctt | gcg | aga | aga | agg | aag | ttg | att | aaa | gat | tta | att | aaa | agc | ctt |     | 3294 |
| Leu | Ala | Arg | Arg | Arg | Lys | Leu | Ile | Lys | Asp | Leu | Ile | Lys | Ser | Leu |     |      |
|1085 |     |     |     |1090 |     |     |     |1095 |     |     |     |     |     |     |     |      |
| cct | ggg | tat | gca | gac | tat | gag | tta | gcg | tgc | cgt | aat | ctt | tat | gga |     | 3339 |
| Pro | Gly | Tyr | Ala | Asp | Tyr | Glu | Leu | Ala | Cys | Arg | Asn | Leu | Tyr | Gly |     |      |
|1100 |     |     |     |1105 |     |     |     |1110 |     |     |     |     |     |     |     |      |
| gtt | taa |     |     |     |     |     |     |     |     |     |     |     |     |     |     | 3345 |
| Val |     |     |     |     |     |     |     |     |     |     |     |     |     |     |     |      |

<210> SEQ ID NO 12
<211> LENGTH: 1114
<212> TYPE: PRT
<213> ORGANISM: Bacillus species R (CAMB2669)

<400> SEQUENCE: 12

Met Asn Asn Ser Glu Lys Gln Val Glu Leu Ala Arg Glu Cys Ile Ile
1               5                   10                  15

Ala Ser Leu Gly Leu Ile Arg Gly Gly Lys Val Glu Asp Val Ile Arg
                20                  25                  30

His Ser Phe Thr Ser Tyr Leu Arg Thr Met Phe Pro Asp Glu Pro Ser
            35                  40                  45

Trp Ile Lys Gln His Ile Glu Gly Ser Glu Ser Ala Val Lys Phe Ser
        50                  55                  60

Lys Glu Gly Lys Leu Arg Thr Gly Phe Val Asp Asn Leu Val Asp Leu
65                  70                  75                  80

Thr Ala Ile Glu Tyr Glu Ser Asn Ile Thr Asn Lys Thr Lys Phe Glu
                85                  90                  95

Asn Gly Tyr Gly Gln Val Lys Asp Tyr Cys Ala Ser Leu Leu Asn Lys
            100                 105                 110

Gly Tyr Asp Ser Glu Leu Ile Leu Gly Val Leu Ser Asp Thr Val Arg

-continued

```
            115                 120                 125
Trp Lys Ala Tyr Lys Ile Lys Thr Ile Val Thr Pro Ala Asn Arg Lys
        130                 135                 140
Phe Gly Arg Asp Asp Ile Glu Leu Asp Glu Ile Glu Ser Ile Asp Leu
145                 150                 155                 160
Ser Leu Ala Asp Asn Leu Ala Gly Lys Arg Leu Ile Asp Phe Leu Asn
                165                 170                 175
Thr Tyr Leu Gly Arg Leu Gly Ser Arg Pro Leu Thr Ala Ser Ser Leu
            180                 185                 190
Ala Asn Asp Leu Gly Phe Asp Ser His Phe Cys Ser Arg His Ile Ser
        195                 200                 205
Ser Leu Arg Glu Leu Val Asn Asn Ala Phe Thr Gln Arg Pro Glu Tyr
        210                 215                 220
Gly Glu Met Ile Thr Asn Leu Trp Cys Arg Phe Val Ser Tyr Leu Arg
225                 230                 235                 240
Asp Lys Asn Ser Val Ala Glu Phe Asp Arg Glu Met Tyr Ser Asp Glu
                245                 250                 255
Leu Tyr Ile Leu Thr Leu Ala Lys Leu Val Cys Ala Asn Ile Ile Glu
            260                 265                 270
Asn Arg Ala Leu Arg Ser Asp Arg Asp Glu Ile Ser Ala Ile Met Gln
        275                 280                 285
Gly Asp Phe Phe Lys Val Arg Gly Ile Met Asn Leu Val Glu Tyr Asp
    290                 295                 300
Tyr Phe Gly Trp Leu Asn Glu Gly Glu Phe Leu Glu Lys Ile Ile Pro
305                 310                 315                 320
Val Ala Gln Glu Met Gln Glu Asp Leu Met Ala Tyr Asn Phe Ser Ala
                325                 330                 335
Pro Pro Ala Asp Asp Leu Phe Gly Gln Ile Met Ala Gln Leu Ala Ser
            340                 345                 350
Arg Ser Gln Arg Ile Leu Leu Gly Gln Glu Trp Thr Pro Lys Trp Leu
        355                 360                 365
Ala Ser Ser Ile Val Lys Gln Val Leu Glu Lys Leu Pro Val Glu Glu
    370                 375                 380
Phe Pro Lys Leu Val Asp Met Cys Cys Gly Ser Gly Ala Leu Ile Val
385                 390                 395                 400
Glu Ala Ile Glu Gln Ser Lys Ala Met Ile Lys Arg Asn Lys Ile Thr
                405                 410                 415
Ser Gln Ser Ser Ile Gly Leu Asp Pro Thr Asn Gly Ser Ser Gly Met
                420                 425                 430
Leu Ile Lys Ser Ile Glu Ala Thr Gln Cys Leu Asn Glu Ile Glu Ile
            435                 440                 445
Asp Gln Ala Glu Ile Glu Leu Leu Thr Gln Ala Ile Thr Gly Phe Asp
    450                 455                 460
Ile Asp Pro Leu Ala Val Met Leu Ser Lys Ile Ser Trp Leu Leu Ala
465                 470                 475                 480
Ala Arg Asp Trp Leu Glu Pro Phe Gly Ser Phe Glu Val Thr Ile Pro
                485                 490                 495
Val Tyr His Ala Asp Ser Leu Phe Ala Ile Thr Pro Leu Ser Asp Val
            500                 505                 510
Ile Gly Glu Glu Glu Gln Glu Asp Cys Tyr Gln Leu Gln Ile Ala Glu
        515                 520                 525
Asp Leu Ile Lys Leu Pro Lys Phe Leu Ile Ser Pro Gln Phe Leu Asn
        530                 535                 540
```

-continued

```
Tyr Phe Asp Thr Leu Ile Asp Phe Gly Tyr Asn Ile Ala Ile Thr Ile
545                 550                 555                 560

Gly Met Ile Glu Asp Arg Glu Leu Glu Ser Phe Val Ser Ala Thr Leu
            565                 570                 575

Asn Asp Ser Glu Leu Glu Val Asp Ser Ala Met Ile Val Ser Thr Lys
        580                 585                 590

Arg Phe Leu Ser Ser Phe Ile Ser Thr Val Ser Arg Leu His Ser Glu
    595                 600                 605

Gly Arg Asn Gly Ile Trp Ala Phe Ile Leu Arg Asn Ser Tyr Arg Pro
610                 615                 620

Gly Leu Val Ala Gly Gln Phe Asn Gly Leu Val Ser Asn Pro Pro Trp
625                 630                 635                 640

Leu Ala Leu Ser Lys Ile Glu Asn Asn Pro Tyr Gln Gln Val Leu Lys
            645                 650                 655

Lys Lys Ala Glu Arg Phe Gly Ile Lys Pro Pro Gly Pro Ala Phe Leu
        660                 665                 670

His Ile Glu Met Ala Thr Thr Phe Leu Leu His Ala Val Asp Arg Tyr
    675                 680                 685

Leu Lys Ser Gly Ala Val Val Gly Cys Ile Thr Pro Glu Thr Val Leu
690                 695                 700

Asn Gly Tyr Asn His Glu Pro Phe Arg Gln Leu Ala Phe Ser Lys Thr
705                 710                 715                 720

Ala Asn Pro Val Asn Phe Glu Leu Asn Glu Ile Trp Lys Leu Glu Glu
            725                 730                 735

Asn Thr Phe Lys Asn Lys Gly Ile Val Leu Phe Gly Thr Lys Ser Asn
        740                 745                 750

Ser Ser Pro Val Leu Pro Asn Pro Ile Pro Gly Ala Val Val Gly Lys
    755                 760                 765

Asn Ser Leu Ser Ile Thr Ser Phe Phe Met Asn Thr Gln Gly Lys Arg
770                 775                 780

Ser Ala Leu Ser Asp Asn Gln Thr Asn Arg Asp Asn Lys Ala Ser Leu
785                 790                 795                 800

Ser Pro Gly Ser Phe Lys Gln Gly Ala Asp Asn Met Pro Arg Arg Leu
            805                 810                 815

Leu Phe His Glu Ile Thr Pro Ile Lys Ser Ala Lys Gly Ile Gln Gln
        820                 825                 830

Val Ser Val Lys Pro Ile Glu Val Gly Val Ser Pro Leu Ser Phe Ile
    835                 840                 845

Val Lys Asp Ala Lys Lys Leu Ser Asp Phe Arg Ile Asn Pro Thr Val
850                 855                 860

Leu Pro Ser Asp Leu Phe Tyr Asp Val Leu Thr Ser Asn Met Leu Thr
865                 870                 875                 880

Pro Phe Asn Ile Val Ser Pro Val Lys Ala Leu Leu Pro Ile Arg Arg
            885                 890                 895

Gly Ser Asn Asp Lys Trp Glu Pro Leu Thr Glu Gly Ser Leu Ile Ala
        900                 905                 910

Lys Gly Gln Arg Val Asn Leu Ala Phe Lys Gln Ile Phe Ser Ala Met
    915                 920                 925

Gly Asn Lys Ala Asp Ile Asn Thr Leu Trp Asn Gln Ile Asn Thr Arg
930                 935                 940

Gly Lys Leu Ala Gln Gln Val Ile Gln Pro Gly Gly Tyr Leu Leu Phe
945                 950                 955                 960
```

-continued

```
Thr Gly Thr Ser Gly Glu Lys Val Cys Ser Ala Phe Leu Asp Thr Gln
                965                 970                 975

Lys Ile Asp Ile Glu Arg Leu Ile Ile Asp Gln Thr Leu Asn Trp Ala
        980                 985                 990

Thr Val Glu Thr Leu Asp Glu Ala Cys Tyr Ile Thr Gly Leu Phe Asn
            995                1000                1005

Ser Glu Ala Ile Asn Leu Met Ile Lys Asp Phe Gln Pro Glu Gly
    1010                1015                1020

Ala Phe Gly Gly Arg His Ile His Ser Leu Pro Phe Arg Val Thr
    1025                1030                1035

Pro Arg Phe Asp Ser Thr Gln Pro Ala His Gln Glu Val Val Glu
    1040                1045                1050

Lys Thr Lys Phe Leu Ile Met Glu Phe Gln Gly Leu Lys His Ser
    1055                1060                1065

Asp Pro Thr Ile Glu Glu Asn Leu Leu Asn Pro Asn Phe Ser Thr
    1070                1075                1080

Leu Ala Arg Arg Arg Lys Leu Ile Lys Asp Leu Ile Lys Ser Leu
    1085                1090                1095

Pro Gly Tyr Ala Asp Tyr Glu Leu Ala Cys Arg Asn Leu Tyr Gly
    1100                1105                1110

Val

<210> SEQ ID NO 13
<211> LENGTH: 35
<212> TYPE: PRT
<213> ORGANISM: Bacillus species R (CAMB2669)
<220> FEATURE:
<221> NAME/KEY: MISC_FEATURE
<222> LOCATION: (34)..(34)
<223> OTHER INFORMATION: X=any amino acid
<221> NAME/KEY: MISC_FEATURE
<222> LOCATION: (14)..(14)
<223> OTHER INFORMATION: X=cysteine or serine

<400> SEQUENCE: 13

Met Asn Asn Ser Glu Lys Gln Val Glu Leu Ala Arg Glu Xaa Ile Ile
1               5                  10                  15

Ala Ser Leu Gly Leu Ile Arg Gly Gly Lys Val Glu Asp Val Ile Arg
            20                  25                  30

His Xaa Phe
        35

<210> SEQ ID NO 14
<211> LENGTH: 37
<212> TYPE: PRT
<213> ORGANISM: Bacillus species R (CAMB2669)

<400> SEQUENCE: 14

Met Asn Asn Ser Glu Lys Gln Val Glu Leu Ala Arg Glu Cys Ile Ile
1               5                  10                  15

Ala Ser Leu Gly Leu Ile Arg Gly Gly Lys Val Glu Asp Val Ile Arg
            20                  25                  30

His Ser Phe Thr Ser
        35

<210> SEQ ID NO 15
<211> LENGTH: 15
<212> TYPE: PRT
<213> ORGANISM: Bacillus species R (CAMB2669)
```

```
<400> SEQUENCE: 15

Met Asn Glu Val Arg Val Arg Tyr Ala Pro Ser Pro Thr Gly His
1               5                   10                  15

<210> SEQ ID NO 16
<211> LENGTH: 35
<212> TYPE: PRT
<213> ORGANISM: Bacillus species R (CAMB2669)
<220> FEATURE:
<221> NAME/KEY: MISC_FEATURE
<222> LOCATION: (14)..(14)
<223> OTHER INFORMATION: X=cysteine or serine
<221> NAME/KEY: MISC_FEATURE
<222> LOCATION: (34)..(34)
<223> OTHER INFORMATION: X=any amino acid

<400> SEQUENCE: 16

Met Asn Asn Ser Glu Lys Gln Val Glu Leu Ala Arg Glu Xaa Ile Ile
1               5                   10                  15

Ala Ser Leu Gly Leu Ile Arg Gly Gly Lys Val Glu Asp Val Ile Arg
            20                  25                  30

His Xaa Phe
        35

<210> SEQ ID NO 17
<211> LENGTH: 37
<212> TYPE: PRT
<213> ORGANISM: Bacillus species R (CAMB2669)
<220> FEATURE:
<221> NAME/KEY: MISC_FEATURE
<222> LOCATION: (4)..(4)
<223> OTHER INFORMATION: X=serine or glycine
<221> NAME/KEY: MISC_FEATURE
<222> LOCATION: (14)..(14)
<223> OTHER INFORMATION: X=cysteine or serine

<400> SEQUENCE: 17

Met Asn Asn Xaa Glu Lys Gln Val Glu Leu Ala Arg Glu Xaa Ile Ile
1               5                   10                  15

Ala Ser Leu Gly Leu Ile Arg Gly Gly Lys Val Glu Asp Val Ile Arg
            20                  25                  30

His Ser Phe Thr Ser
        35

<210> SEQ ID NO 18
<211> LENGTH: 20
<212> TYPE: DNA
<213> ORGANISM: synthetic
<220> FEATURE:
<221> NAME/KEY: misc_feature
<222> LOCATION: (6)..(6)
<223> OTHER INFORMATION: Y=C or T
<221> NAME/KEY: misc_feature
<222> LOCATION: (9)..(9)
<223> OTHER INFORMATION: Y=C or T
<221> NAME/KEY: misc_feature
<222> LOCATION: (12)..(12)
<223> OTHER INFORMATION: Y=C or T
<221> NAME/KEY: misc_feature
<222> LOCATION: (15)..(15)
<223> OTHER INFORMATION: R=A or G
<221> NAME/KEY: misc_feature
<222> LOCATION: (18)..(18)
<223> OTHER INFORMATION: R=A or G

<400> SEQUENCE: 18
atgaayaaya gygaraarca                                         20
```

```
<210> SEQ ID NO 19
<211> LENGTH: 20
<212> TYPE: DNA
<213> ORGANISM: synthetic
<220> FEATURE:
<221> NAME/KEY: misc_feature
<222> LOCATION: (6)..(6)
<223> OTHER INFORMATION: Y=C or T
<221> NAME/KEY: misc_feature
<222> LOCATION: (9)..(9)
<223> OTHER INFORMATION: Y=C or T
<221> NAME/KEY: misc_feature
<222> LOCATION: (12)..(12)
<223> OTHER INFORMATION: N=G, A, C, or T
<221> NAME/KEY: misc_feature
<222> LOCATION: (15)..(15)
<223> OTHER INFORMATION: R=A or G
<221> NAME/KEY: misc_feature
<222> LOCATION: (18)..(18)
<223> OTHER INFORMATION: R=A or G

<400> SEQUENCE: 19
atgaayaayt cngaraarca                                               20

<210> SEQ ID NO 20
<211> LENGTH: 7
<212> TYPE: PRT
<213> ORGANISM: synthetic

<400> SEQUENCE: 20

Met Asn Asn Ser Glu Lys Gln
1               5

<210> SEQ ID NO 21
<211> LENGTH: 17
<212> TYPE: DNA
<213> ORGANISM: synthetic
<220> FEATURE:
<221> NAME/KEY: misc_feature
<222> LOCATION: (3)..(3)
<223> OTHER INFORMATION: N=G, A, C or T
<221> NAME/KEY: misc_feature
<222> LOCATION: (6)..(6)
<223> OTHER INFORMATION: R=A or G
<221> NAME/KEY: misc_feature
<222> LOCATION: (9)..(9)
<223> OTHER INFORMATION: Y=C or T
<221> NAME/KEY: misc_feature
<222> LOCATION: (12)..(12)
<223> OTHER INFORMATION: N=G, A, C or T
<221> NAME/KEY: misc_feature
<222> LOCATION: (15)..(15)
<223> OTHER INFORMATION: Y=C or T

<400> SEQUENCE: 21
atnacrtcyt cnacytt                                                  17

<210> SEQ ID NO 22
<211> LENGTH: 6
<212> TYPE: PRT
<213> ORGANISM: Bacillus species R (CAMB2669)

<400> SEQUENCE: 22

Ile Val Asp Glu Val Lys
1               5

<210> SEQ ID NO 23
<211> LENGTH: 37
<212> TYPE: PRT
<213> ORGANISM: Bacillus species R (CAMB2669)
```

```
<400> SEQUENCE: 23

Met Asn Asn Ser Glu Lys Gln Val Glu Leu Ala Arg Glu Cys Ile Ile
1               5                   10                  15

Ala Ser Leu Gly Leu Ile Arg Gly Gly Lys Val Glu Asp Val Ile Arg
            20                  25                  30

His Ser Phe Thr Ser
            35

<210> SEQ ID NO 24
<211> LENGTH: 24
<212> TYPE: DNA
<213> ORGANISM: synthetic

<400> SEQUENCE: 24
gattatacac tctctagcta gctc                                            24

<210> SEQ ID NO 25
<211> LENGTH: 26
<212> TYPE: DNA
<213> ORGANISM: synthetic

<400> SEQUENCE: 25
gctagtttgg gcttaattcg aggggg                                          26

<210> SEQ ID NO 26
<211> LENGTH: 24
<212> TYPE: DNA
<213> ORGANISM: synthetic

<400> SEQUENCE: 26
atttgtgagt tacctaagag ataa                                            24

<210> SEQ ID NO 27
<211> LENGTH: 24
<212> TYPE: DNA
<213> ORGANISM: synthetic

<400> SEQUENCE: 27
ctacaccata gattagtaat catt                                            24

<210> SEQ ID NO 28
<211> LENGTH: 20
<212> TYPE: DNA
<213> ORGANISM: synthetic

<400> SEQUENCE: 28
tctaaatgaa atagaaattg                                                 20

<210> SEQ ID NO 29
<211> LENGTH: 21
<212> TYPE: DNA
<213> ORGANISM: synthetic

<400> SEQUENCE: 29
cattgtgttg cctctatcga t                                               21

<210> SEQ ID NO 30
<211> LENGTH: 24
<212> TYPE: DNA
<213> ORGANISM: synthetic

<400> SEQUENCE: 30
```

-continued

```
ctctatcctc aatcattcca attg                                              24

<210> SEQ ID NO 31
<211> LENGTH: 24
<212> TYPE: DNA
<213> ORGANISM: synthetic

<400> SEQUENCE: 31
ttgagagctt tgttagtgct acct                                              24

<210> SEQ ID NO 32
<211> LENGTH: 21
<212> TYPE: DNA
<213> ORGANISM: synthetic

<400> SEQUENCE: 32
gaataatccc taccaacagg t                                                 21

<210> SEQ ID NO 33
<211> LENGTH: 21
<212> TYPE: DNA
<213> ORGANISM: synthetic

<400> SEQUENCE: 33
tctatcttgc ttagagctag c                                                 21

<210> SEQ ID NO 34
<211> LENGTH: 24
<212> TYPE: DNA
<213> ORGANISM: synthetic

<400> SEQUENCE: 34
gaccttgtgg gtgaataagg aaac                                              24

<210> SEQ ID NO 35
<211> LENGTH: 24
<212> TYPE: DNA
<213> ORGANISM: synthetic

<400> SEQUENCE: 35
gagaagttag catcaataac tgta                                              24

<210> SEQ ID NO 36
<211> LENGTH: 23
<212> TYPE: DNA
<213> ORGANISM: synthetic

<400> SEQUENCE: 36
tacagcctct tctgtaattg atc                                               23

<210> SEQ ID NO 37
<211> LENGTH: 24
<212> TYPE: DNA
<213> ORGANISM: synthetic

<400> SEQUENCE: 37
cttccttctg caattgttgc tagc                                              24

<210> SEQ ID NO 38
<211> LENGTH: 21
<212> TYPE: DNA
<213> ORGANISM: synthetic
```

-continued

```
<400> SEQUENCE: 38
aagggaataa ctcatgccca t                                              21

<210> SEQ ID NO 39
<211> LENGTH: 24
<212> TYPE: DNA
<213> ORGANISM: synthetic

<400> SEQUENCE: 39
gtgatatcct gctctatata aatc                                           24

<210> SEQ ID NO 40
<211> LENGTH: 27
<212> TYPE: DNA
<213> ORGANISM: synthetic

<400> SEQUENCE: 40
gtgttcagat tgtaacaaag aagtagc                                        27

<210> SEQ ID NO 41
<211> LENGTH: 24
<212> TYPE: DNA
<213> ORGANISM: synthetic

<400> SEQUENCE: 41
acgtcactcc aaatactgtg tcga                                           24

<210> SEQ ID NO 42
<211> LENGTH: 51
<212> TYPE: DNA
<213> ORGANISM: synthetic

<400> SEQUENCE: 42
tatatcgcat gcggaggtaa aaaatgaag ggaaatcaga taatagacaa c              51

<210> SEQ ID NO 43
<211> LENGTH: 39
<212> TYPE: DNA
<213> ORGANISM: synthetic

<400> SEQUENCE: 43
gtcgacgcat gcttatttat ttctaaaaga aagcttttc                           39

<210> SEQ ID NO 44
<211> LENGTH: 39
<212> TYPE: DNA
<213> ORGANISM: synthetic

<400> SEQUENCE: 44
ggagagaatc atatgaacaa tagtgaaaag caagttgag                           39

<210> SEQ ID NO 45
<211> LENGTH: 36
<212> TYPE: DNA
<213> ORGANISM: synthetic

<400> SEQUENCE: 45
ctaggatcct taaactccat aaagattacg gcacgc                              36
```